(12) United States Patent
Kuroita et al.

(10) Patent No.: US 7,601,504 B2
(45) Date of Patent: Oct. 13, 2009

(54) PROTEIN ACHIEVING IMPROVED BLOCKING EFFICIENCY

(75) Inventors: Toshihiro Kuroita, Tsuruga (JP); Atsushi Sogabe, Otsu (JP); Yutaka Takarada, Tsuruga (JP); Naoki Tanaka, Kyoto (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 343 days.

(21) Appl. No.: 10/562,776

(22) PCT Filed: Jul. 2, 2004

(86) PCT No.: PCT/JP2004/009785

§ 371 (c)(1),
(2), (4) Date: Dec. 29, 2005

(87) PCT Pub. No.: WO2005/003155

PCT Pub. Date: Jan. 13, 2005

(65) Prior Publication Data

US 2006/0183173 A1    Aug. 17, 2006

(30) Foreign Application Priority Data

Jul. 3, 2003   (JP) .............................. 2003-191081

(51) Int. Cl.
*G01N 33/53* (2006.01)
(52) U.S. Cl. ...................... 435/7.1; 435/7.21; 436/501; 436/518
(58) Field of Classification Search ...................... None
See application file for complete search history.

(56) References Cited

U.S. PATENT DOCUMENTS 5,399,500 A    3/1995  Oppenheimer et al.

FOREIGN PATENT DOCUMENTS

EP    0 575 998 A1    12/1993
JP    6-66803 A       3/1994

OTHER PUBLICATIONS

Chesnokova et al. (Biochemistry, Aug. 5, 2003, vol. 42, No. 30, pp. 9028-9040).*
Zhang et al. (Journal of Biological Chemistry, 1996, vol. 271., No. 33, pp. 19668-19674).*
Swain et al. (Biochemical Society symposium, 2001, No. 68., pp. 69-82).*
Boice et al.(Journal of Biological Chemistry, 1997, vol. 272, No. 40, pp. 24825-24831).*
Zhang and Walker (Archives of Biochemistry and Biophysics, Aug. 15, 1998, vol. 356, No. 2, pp. 177-186).*
Peterfi et al., *J. Immunoassay*, 21(4): 341-354 (Nov. 2000).
Gragerov et al., *J. Mol. Biol.*, 235: 848-854 (1994).
Janssen et al., *Biomaterials*, 23: 4847-4854 (2002).
Morshauser et al., *J. Mol. Biol.*, 289: 1387-1403 (1999).
Scholtmeijer et al., *Applied and Environmental Microbiology*, 68(3): 1367-1373 (Mar. 2002).
Tanaka et al., *Proc. Natl. Acad. Sci.*, 99(24): 15398-15403 (Nov. 26, 2002).
Wang et al., *Biochemistry*, 37: 7929-7940 (1998).
Zhu et al., *Science*, 272: 1606-1614 (Jun. 14, 1996).

* cited by examiner

*Primary Examiner*—Lisa V Cook
(74) *Attorney, Agent, or Firm*—Leydig, Voit & Mayer, Ltd.

(57) ABSTRACT

It is intended to provide a method of conveniently screening a novel protein or a novel partial sequence protein having a blocking ability based on amino acid sequence data; and a protein achieving an improved blocking efficiency that can be expressed on a large scale in *Escherichia coli*. A method of screening a novel protein or a novel partial sequence protein having a blocking ability based on amino acid sequence data; a protein characterized by achieving an improved blocking efficiency owing to an amino acid sequence modification; and a method of utilizing the protein.

20 Claims, 17 Drawing Sheets

Fig.13

| | BSA | α Casein | Lipase |
|---|---|---|---|
| Hydrophilic amino acid content | 0.37 | 0.34 | 0.21 |
| Hydrophobic amino acid content | 0.41 | 0.45 | 0.51 |
| Hydrophilic/hydrophobic rate | 0.90 | 0.76 | 0.41 |
| Blocking ability | Good | Good | Poor |

Fig. 14

| | BSA | | | α Casein | | | Lipase | | | DnaK 384-607 | | |
|---|---|---|---|---|---|---|---|---|---|---|---|---|
| | N terminal side | C terminal side | Full length | N terminal side | C terminal side | Full length | N terminal side | C terminal side | Full length | N terminal side | C terminal side | Full length |
| Hydrophilic amino acid content | 0.40 | 0.35 | 0.37 | 0.37 | 0.30 | 0.34 | 0.22 | 0.20 | 0.21 | 0.25 | 0.37 | 0.29 |
| Hydrophobic amino acid content | 0.40 | 0.42 | 0.41 | 0.42 | 0.47 | 0.45 | 0.57 | 0.45 | 0.51 | 0.50 | 0.41 | 0.45 |
| Hydrophilic/hydrophobic rate | 1.00 | 0.83 | 0.90 | 0.88 | 0.64 | 0.76 | 0.39 | 0.44 | 0.41 | 0.50 | 0.90 | 0.64 |
| $|\Delta|$ | 0.17 | | — | 0.24 | | — | 0.05 | | — | 0.40 | | — |

Fig.15

Example 7 Comparison of blocking effects of (native) DnaK fragment without His tag and BSA

| PEO131 Dilution ratio | High concentration | | | Low concentration | | |
|---|---|---|---|---|---|---|
| | Commercially available goods A 10mg/ml | Commercially available goods B 10mg/ml | DnaK 419-607 0.5mg/ml | Commercially available goods A 2mg/ml | Commercially available goods B 2mg/ml | DnaK 419-607 0.1mg/ml |
| 40 | 0.016 | 0.024 | 0.013 | 0.068 | 0.094 | 0.086 |
| 80 | 0.007 | 0.012 | 0.007 | 0.036 | 0.046 | 0.069 |
| 160 | 0.004 | 0.005 | 0.005 | 0.017 | 0.021 | 0.024 |
| 320 | 0.005 | 0.004 | 0.003 | 0.012 | 0.013 | 0.014 |

Values in Table: Absorbance at 450 nm (Abs)

PROTEIN ACHIEVING IMPROVED BLOCKING EFFICIENCY

CROSS-REFERENCE TO RELATED APPLICATIONS

This patent application is the U.S. national phase of International Patent Application PCT/JP04/09785, filed on Jul. 2, 2004, which claims the benefit of Japanese Patent Application No. 2003-191081, filed on Jul. 3, 2003.

TECHNICAL FIELD

The present invention relates to a method of screening a novel protein or a novel partial sequence protein candidate for blocking having a blocking ability based on amino acid sequence data, and further relates to a protein achieving an improved blocking efficiency by modifying an amino acid sequence of a protein. The present invention also relates to a blocking reagent, a stabilizing agent, an excipient, a protein folding accelerator, a protein refolding accelerator and a coating agent for medical use, which contain the protein. The present invention can improve the blocking efficiency of a protein capable of being expressed on a large scale in *Escherichia coli*, and is useful when a recombinant protein excellent in blocking efficiency is produced on a large scale.

BACKGROUND ART

Conventionally, proteins directly extracted from living body components have been often used as blocking agents used for immunoassays. In particular historically, albumin and casein derived from bovine have been widely used. However, recently, various limitations have occurred owing to problems such as mad cow disease. Meanwhile, method of producing them using recombinant technology has an advantage that a pathogen (substance) can be excluded, but is virtually off from practical use due to problems such as productivity.

Accordingly, it can be said that an attempt to use a protein derived from *Escherichia coli* as an alternative protein is preferable in terms of productivity. However, there has been a problem in that a protein capable of being expressed on a large scale does not always have a good blocking efficiency and a protein which can be produced by recombinant technology and is excellent in blocking efficiency must be found.

Recently, gene sequences in various organisms have been elucidated, but a principle to find a protein excellent in blocking efficiency by a predicted amino acid sequence has not be known yet, and it has seemed that it takes a lot of trouble to search such a protein.

Due to such reasons, an alternative protein which can be produced on a large scale by recombinant technology and is excellent in blocking efficiency has been required.

BRIEF DESCRIPTION OF THE DRAWINGS

In FIG. 5, Blank: no blocking
384-638: DnaK 384-638
384-607: DnaK 384-607
384-578: DnaK 384-578, a mutant where a part of the α-helix structure was deleted.
384-561: DnaK 384-561, a mutant where about a half of the α-helix structure was deleted.
508-607: DnaK 508-607, a mutant where the β-sheet portion was deleted (composed of the α-helix).
525-607: DnaK 525-607, a mutant where the β-sheet portion and a part of the α-helix were deleted (composed of the α-helix).
BSA: BSA fraction V

384-607: DnaK 384-607
384-607 (VAV): DnaK 384-607 (D479V, S481V)
419-607: DnaK 419-607
BSA: BSA fraction V
Blank: no blocking

FIG. 13 shows content rates of hydrophilic and hydrophobic amino acids in proteins frequently used for blocking and a highly hydrophobic protein.

FIG. 14 shows characteristics of amino acids contained in the N terminal side and C terminal side of BSA, α-casein, lipase and DnaK 384-607. |Δ| represents an absolute value of a difference between hydrophilic/hydrophobic rates in the N terminal side and the C terminal side.

FIG. 15 shows comparison of blocking effects of a (native) DnaK fragment without histidine tag. BSA (fraction V) and the DnaK 419-607 fragment were prepared at concentrations of 10 mg/mL and 0.5 mg/mL, respectively, and shown as the comparison at high concentrations. BSA (fraction V) and the DnaK 419-607 fragment also were prepared at concentrations of 2 mg/mL and 0.1 mg/mL, respectively, and shown as the comparison at low concentrations.

DISCLOSURE OF THE INVENTION

Figure 1:
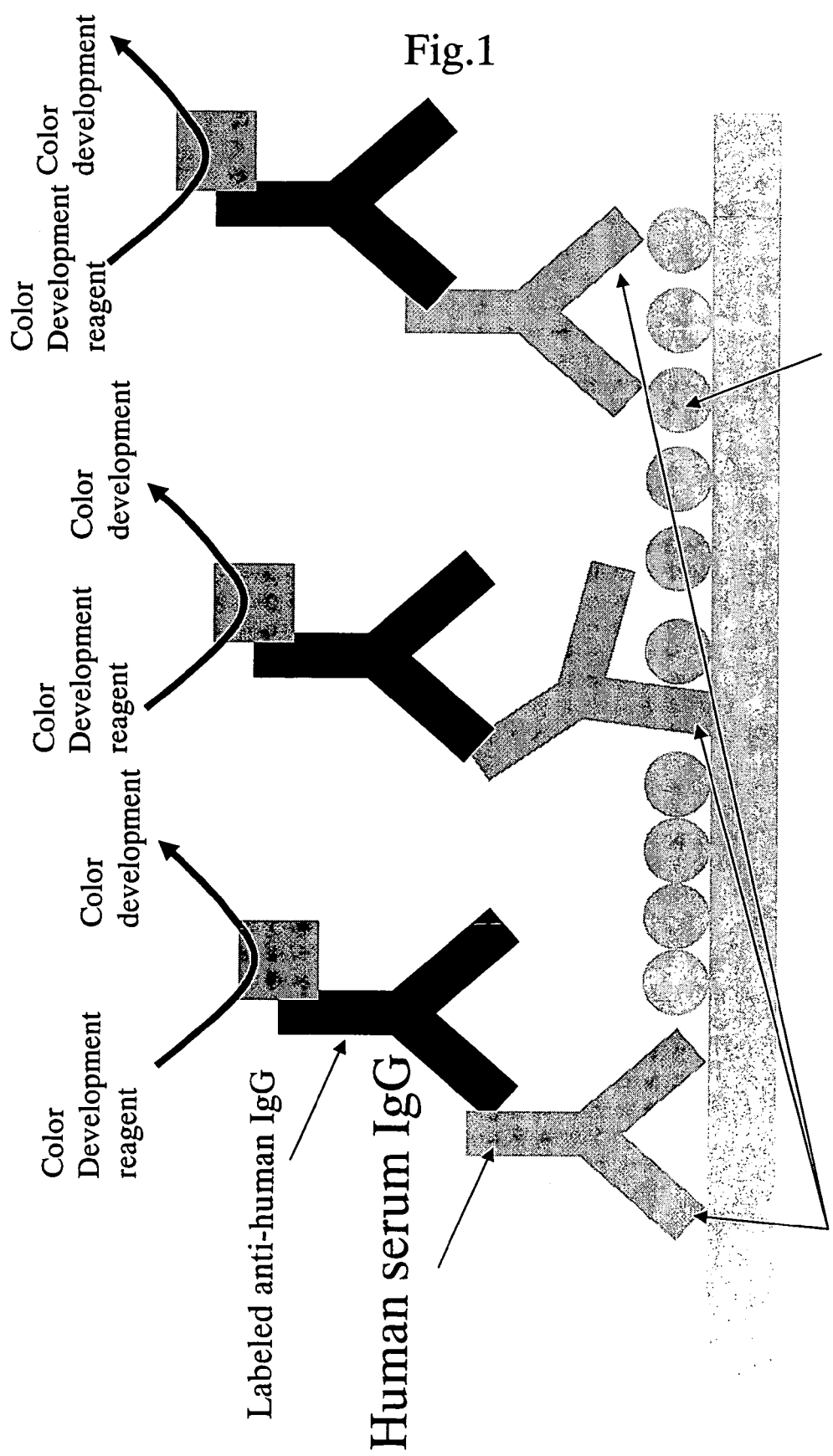
FIG. 1 is a view showing a concept of measuring a blocking efficiency.

An object of the present invention is to provide a method of easily finding a protein having a blocking ability from an amino acid sequence, as well as provide a protein which can be produced in *Escherichia coli* on a large scale and achieves an improved blocking efficiency by modification of the amino acid sequence.

Based on the above context, as a result of an extensive study, a character concerning an amino acid sequence characteristic for a protein having a blocking ability has been found, as well as it has been found that a blocking efficiency can be dramatically enhanced by modifying an amino acid sequence of the protein found in such a way to complete the present invention.

That is, the present invention is composed of the following constitution.

[1] A method of screening a novel protein or a novel partial sequence protein candidate for blocking having a blocking ability based on amino acid sequence data, the method of screening the protein or the partial sequence protein, which meets the following conditions:
A) the amino acid sequence of the protein is divided into two, and an absolute value of a difference between hydrophilic/hydrophobic rates in divided two portions is 0.1 or more, calculated using the following formula from content rates of hydrophilic amino acids (D, E, K, H, R, Y) and hydrophobic amino acids (G, A, V, L, I, M, F, W, P); [Hydrophilic/hydrophobic rate]=[Content rate of hydrophilic amino acids]/[Content rate of hydrophobic amino acids];
B) the hydrophilic/hydrophobic rate in a hydrophilic portion (a higher value of hydrophilic/hydrophobic rate) is 0.5 or more; and
C) the protein is composed of more than 100 amino acid residues.

[2] A novel protein or a novel partial sequence protein for blocking having a blocking ability, screened by the method of [1], the protein or the partial sequence protein which can be obtained by the following analysis step D and meets the following condition E;
D) (1) a step of adding a candidate protein (0.5 to 1 mg/mL, diluted with 20 mM Tris-HCl, pH 7.0) which meets the conditions of [1] and bovine serum albumin (fraction V) prepared by the same way to respective wells of a polystyrene immunotiter plate, blocking at 2 to 10° C. for 4 to 5 hours and removing solutions;
(2) a step of adding normal human serum diluted 25 to 100 times with PBS(−), leaving stand at 37° C. for one hours, and subsequently washing the plate with PBS(−) (0.05% TWEEN® (polysorbate) 20); and
(3) a step of comparing IgG amounts non-specifically absorbed to the plate using an enzyme-labeled anti-human IgG antibody by a calorimetric method using a chromogenic substrate; and
E) the absorbance for the candidate protein is 2.5 times or less than the developed color intensity for bovine serum albumin.

[3] A novel protein or a novel partial sequence protein for blocking having a blocking ability, screened by the method of [1], the protein or the partial sequence protein which can be obtained by the following analysis step F and meets the following condition G;
F) (1) a step of dissolving horseradish peroxidase for labeling at 0.05 mg/mL in a candidate protein solution (0.5 to 1 mg/mL, diluted with PBS(−)) and a bovine serum albumin (fraction V) solution prepared by the same way;
(2) a step of dispensing the above diluted solutions to a polystyrene 96-well microplate;
(3) a step of leaving stand at 25° C. for one hour, removing the solutions and washing with PBS(−) containing 0.02% TWEEN® (polysorbate) 20;
(4) a step of adding a tetramethylbenzidine solution, incubating at 37° C. and subsequently adding 1N sulfuric acid to stop a reaction and develop a color; and
(5) a step of measuring the absorbance by a microplate reader; and
G) the absorbance for the candidate protein is 2.5 times or less than the developed color intensity for bovine serum albumin.

[4] A novel protein or a novel partial sequence protein for blocking having a blocking ability, screened by the method of [1], the protein or the partial sequence protein which can be obtained by the following analysis step H and meets the following condition I;
H) (1) a step of adding a candidate protein (0.5 to 1 mg/mL, diluted with 20 mM Tris-HCl, pH 7.0) which meets the conditions of [1] and bovine serum albumin (fraction V) prepared by the same way to respective wells of a polystyrene immunotiter plate, blocking at 2 to 10° C. for 4 to 5 hours and removing solutions;
(2) a step of adding a peroxidase solution prepared at 0.05 mg/mL, leaving stand at 37° C. for one hour and subsequently washing the plate with PBS(−) (0.05% TWEEN® (polysorbate)20);
(3) a step of leaving stand at 25° C. for one hour, subsequently removing the solution and washing with PBS(−) containing 0.02% TWEEN® (polysorbate)20; and
(4) a step of adding a tetramethylbenzidine solution, incubating at 37° C. and subsequently adding 1N sulfuric acid to stop a reaction and develop a color; and
(5) a step of measuring the absorbance by a microplate reader; and
I) the absorbance for the candidate protein is 2.5 times or less than the developed color intensity for bovine serum albumin.

[5] A novel protein achieving an improved blocking efficiency by modifying an amino acid sequence of a protein or a partial sequence protein which meets the conditions A, B and C according to [1].

[6] The protein achieving the improved blocking efficiency according to [5] characterized in that the amino acid sequence is modified by amino acid substitution, deletion and insertion.

[7] The protein achieving the improved blocking efficiency according to [5] characterized by being derived from a prokaryotic organism or an eukaryotic organism.

[8] The protein achieving the improved blocking efficiency characterized by being derived from an "HSP 70 family protein".

[9] The protein achieving the improved blocking efficiency according to [8] characterized by being derived from a DnaK protein.

[10] The protein achieving the improved blocking efficiency according to [8] characterized by being a protein obtained by deleting a part of an amino acid sequence of the DnaK protein.

[11] The protein achieving the improved blocking efficiency according to [8], which is a protein obtained by deleting a part of an amino acid sequence of the DnaK protein, characterized in that an amino acid sequence from an N terminus to at least position 387 and at most position 472 has been deleted.

[12] The protein achieving the improved blocking efficiency according to [8], which is a protein obtained by deleting a part of an amino acid sequence of the DnaK protein, characterized in that an amino acid sequence from an N terminus to at least position 387 and at most position 418 has been deleted.

[13] The protein according to [8] composed of an amino acid sequence of positions 419 to 607 in the DnaK protein.

[14] The protein achieving the improved blocking efficiency according to [8] characterized in that a part of hydrophilic amino acids is substituted with hydrophobic amino acids in the DnaK protein wherein an ATPase domain or a part thereof has been deleted.

[15] The protein achieving the improved blocking efficiency according to [8] which is a protein wherein a part of an amino acid sequence is deleted in the DnaK protein wherein an ATPase domain or a part thereof has been deleted, wherein aspartic acid at positions 479 and 481 in the amino acid sequence is substituted with valine.

[16] The protein achieving the improved blocking efficiency according to [8] composed of an amino acid sequence of positions 384 to 607 in the DnaK protein, wherein aspartic acid at positions 479 and 481 in the amino acid sequence has been substituted with valine.

[17] A protein for blocking having one or more hydrophilic domains and one or more hydrophobic domains, wherein the hydrophobic domain can be absorbed to a material surface and the hydrophilic domain can cover the hydrophobic domain absorbed to the material surface.

[18] A modified protein characterized in that a blocking speed is further enhanced than that of BSA.

[19] The modified protein according to [18] characterized in that a blocking ability in less than 10 minutes is more excellent than that of BSA under a condition where protein amounts are adjusted so as to exhibit a blocking efficiency equivalent to that of BSA in blocking for 3 hours.

[20] The protein according any of [2] to [19] characterized by having a tag sequence.

[21] The protein according to [20] characterized in that the tag sequence is selected from a histidine tag, a maltose binding protein (MBP) tag, a glutathione S-transferase (GST) tag, a Flag tag, a Myc tag, and a tandem affinity purification tag.

[22] The protein according to any of claims [2] to [19] characterized in that an optional amino acid sequence is added.

[23] A method of producing a protein characterized by producing the protein according to any of [2] to [22] using a prokaryotic organism.

[24] A method of producing a protein characterized by producing the protein according to any of [2] to [22] using *Escherichia coli*.

[25] A method of producing a protein characterized by producing the protein according to any of [2] to [22] using a cell-free protein synthesis method.

[26] A method of purifying the protein according to any of [2] to [22], characterized by passing through a heating step.

[27] A method of using the protein according to any of [2] to [21] for blocking, stabilization, size enlargement, protein folding promotion, protein refolding promotion, coating and medical use.

[28] A blocking reagent, a stabilizing agent, an excipient, a protein folding accelerator, a protein refolding accelerator, a coating agent for cell attachment or a coating agent for medical use, which contains the protein according to any of [2] to [22].

BEST MODES FOR CARRYING OUT THE INVENTION

As used herein, blocking refers to preventing a component from non-specifically absorbing to a vessel or a carrier, and in particular refers to preventing a protein from non-specifically absorbing to a resin such as plastic. In various measurements, it is problematic that the component subjected to the measurement is non-specifically absorbed to a material surface, which prevents the measurement as a background. Particularly in an immunoassay, an antibody is remarkably absorbed to a polystyrene plate. Typically, a manipulation where the protein easily absorbed to the resin is previously added to prevent non-specific absorption of the antibody, i.e., the blocking is widely performed. In the immunoassay, it is essential to physically absorb the protein to the material surface, and thus, the plate made from the resin such as polystyrene, to which the protein is easily absorbed is often used, but an extra component is also remarkably absorbed. Therefore actually, a good blocking agent is always required. In clinical diagnostic drugs, it is often problematic that an enzyme for the diagnostic drug is non-specifically absorbed to a cell in an automatic analyzer.

In the present invention, with immunoassays in mind, the blocking effect was measured by measuring the non-specific absorption of human serum IgG known as an example of the most remarkable non-specific absorption to the polystyrene plate. That is, the measurement is composed of the following steps.

(1) A protein solution whose blocking ability to be tested is added to a polystyrene 96-well plate, and left stand for a certain time period to block the plate.

(2) The solution in (1) is removed, diluted human serum is added and incubated.

(3) The plate is washed, subsequently a labeled anti-human IgG antibody is added and incubated.

(4) After the plate is washed, amounts of non-specifically bound IgG are compared by a calorimetric method.

The detailed method will be described below. This method was very effective when the present invention was performed. An outline of the method is shown in FIG. 1.

As a blocking agent, conventionally bovine serum albumin (BSA) and bovine milk casein have been widely used. However, it has not been explained theoretically what nature of the protein their high blocking ability is derived from, and generally it is a common belief that hydrophobicity of the protein causes the high binding ability.

Thus first, for the purpose of examining whether a highly hydrophobic protein has the blocking ability, lipase derived from *Pseudomonas aeruginosa*, known for having high contents of hydrophobic amino acids was used as the blocking agent to examine its blocking ability. Lipase is used for clinical laboratory tests, but it has been known that its absorbing ability to a plastic surface is high and the absorption to the cell upon measurement is problematic. However, as a result of the experiment, it was demonstrated that the blocking effect was scarcely observed. Rates of hydrophilic amino acids and hydrophobic amino acids of respective proteins were shown in FIG. 13. Comparing them, it is found that the hydrophobicity of BSA and casein is lower than that of lipase. It is discussed from this that a phenomenon where the protein is absorbed owing to its hydrophobicity is related to the blocking ability but this relation is not explain all cases. As a reason why the blocking ability of lipase was not exerted, it is speculated that the protein was non-specifically absorbed to lipase absorbed to the material surface.

The hydrophilic amino acid and the hydrophobic amino acid referred to herein are variously defined depending on textbooks. In the present invention, as the hydrophilic amino acids, aspartic acid, glutamic acid, lysine, histidine, arginine and tyrosine were defined. Also as the hydrophobic amino acids, glycine, alanine, valine, leucine, isoleucine, methionine, phenylalanine, tryptophan and proline were defined.

In the present invention, as the hydrophilic amino acids, aspartic acid, glutamic acid, lysine, histidine, arginine and tyrosine were defined. Also as the hydrophobic amino acids, glycine, alanine, valine, leucine, isoleucine, methionine, phenylalanine, tryptophan and proline were defined. However, it is thought that among the hydrophilic amino acids, His, Tyr, particularly Tyr are low hydrophilic, and among the hydrophobic amino acids, Gly, Ala, particularly Gly are low hydrophobic. Thus in order to predict more strictly, a good result is sometimes obtained when calculated by excluding Tyr and Gly, and more preferably His, Tyr, Gly and Ala. In modification of the blocking ability shown later, it is preferable to modify with strong and weak of hydrophilicity and hydrophobicity in mind.

Thus subsequently, the content rates of respective amino acids were calculated in various fragments. Consequently, it was demonstrated that the content rates of the hydrophilic amino acids and hydrophobic amino acids tended to be different in each part obtained by dividing an amino acid sequence of BSA (without signal peptide) or bovine a casein (without signal peptide) which exhibit the blocking ability into two, e.g., an N terminal side and a C terminal side (FIG. 14). In the present invention, a value obtained by dividing the content rate of the hydrophilic amino acids by the content rate of the hydrophobic amino acids is conveniently defined as a "hydrophilic/hydrophobic rate". The hydrophilic/hydrophobic rate in the N terminal side of BSA is 1.00 whereas it is 0.83 in the C terminal side. It is found that there is a difference of 0.17. In α casein, the value was 0.88 in the N terminal side whereas it was 0.64 in the C terminal side, and its difference was 0.24. Meanwhile, in lipase derived from *Pseudomonas*, which does not exhibit the blocking ability, the value was 0.39 in the N terminal side whereas it was 0.44 in the C terminal side, and it was found that its difference was 0.05 which was less than 0.1. It was speculated from this that to exhibit the blocking ability, a hydrophilic region is required in addition to a relatively hydrophobic region in a protein molecule.

In the protein of the present invention, it is preferable that the hydrophilic/hydrophobic rate in a hydrophilic portion, a hydrophobic portion and full length are in the following ranges.

The hydrophilic/hydrophobic rate in the hydrophilic portion is 0.5 to 2.0, more preferably 0.7 to 1.7 and still more preferably 0.8 to 1.5.

The hydrophilic/hydrophobic rate in the hydrophobic portion is 0.2 to 1.1, more preferably 0.3 to 1.0 and still more preferably 0.4 to 0.9.

The hydrophilic/hydrophobic rate in the entire protein is 0.4 to 2.0, more preferably 0.5 to 1.5 and still more preferably 0.6 to 1.0.

The difference (absolute value) of the hydrophilic/hydrophobic rates in the hydrophilic portion and the hydrophobic portion is preferably 0.1 to 0.6, more preferably 0.15 to 0.5 and still more preferably 0.15 to 0.4.

The hydrophilic portion and the hydrophobic portion may be either divided two, e.g., the C terminal side (or the N terminal side).

In the present invention, it is supposed that the hydrophilic portion and the hydrophobic portion are present in each portion of divided two, e.g., the C terminal region or the N terminal region. However, those in which the sequence which is neither hydrophilic nor hydrophobic has been added at N terminus or the C terminus are included in the present invention as long as the hydrophilic portion and the hydrophobic portion are present.

Figure 2:
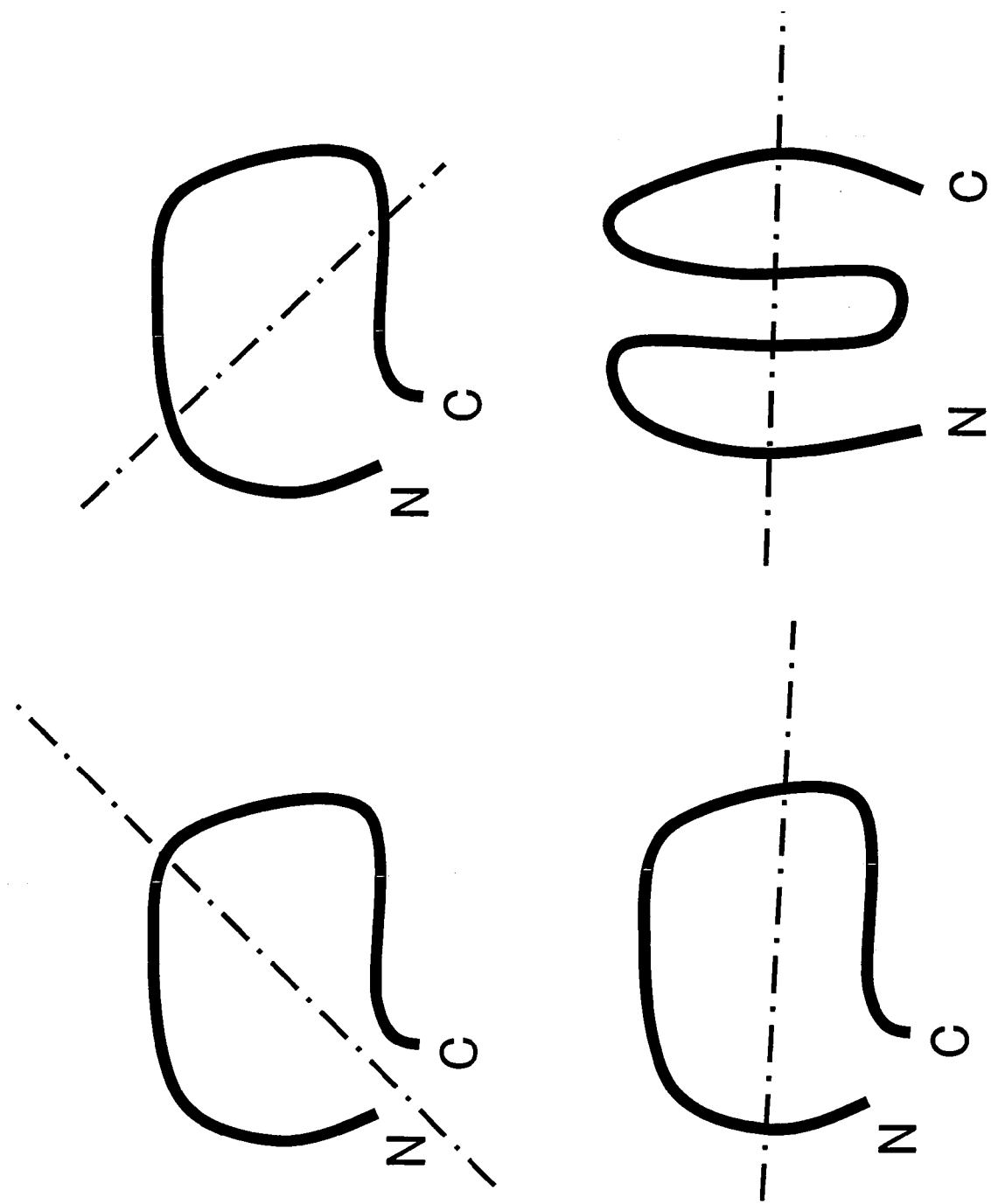
FIG. 2 is a view showing a bisection method of a protein.

Furthermore in the present invention, as shown in FIG. 2, those having respective portions such as the hydrophilic portion-the hydrophobic portion-the hydrophilic portion, the hydrophobic portion-the hydrophilic portion-hydrophobic portion, and the hydrophilic portion-the hydrophobic portion-the hydrophilic portion-the hydrophobic portion in order are also included in the present invention.

Figure 3:
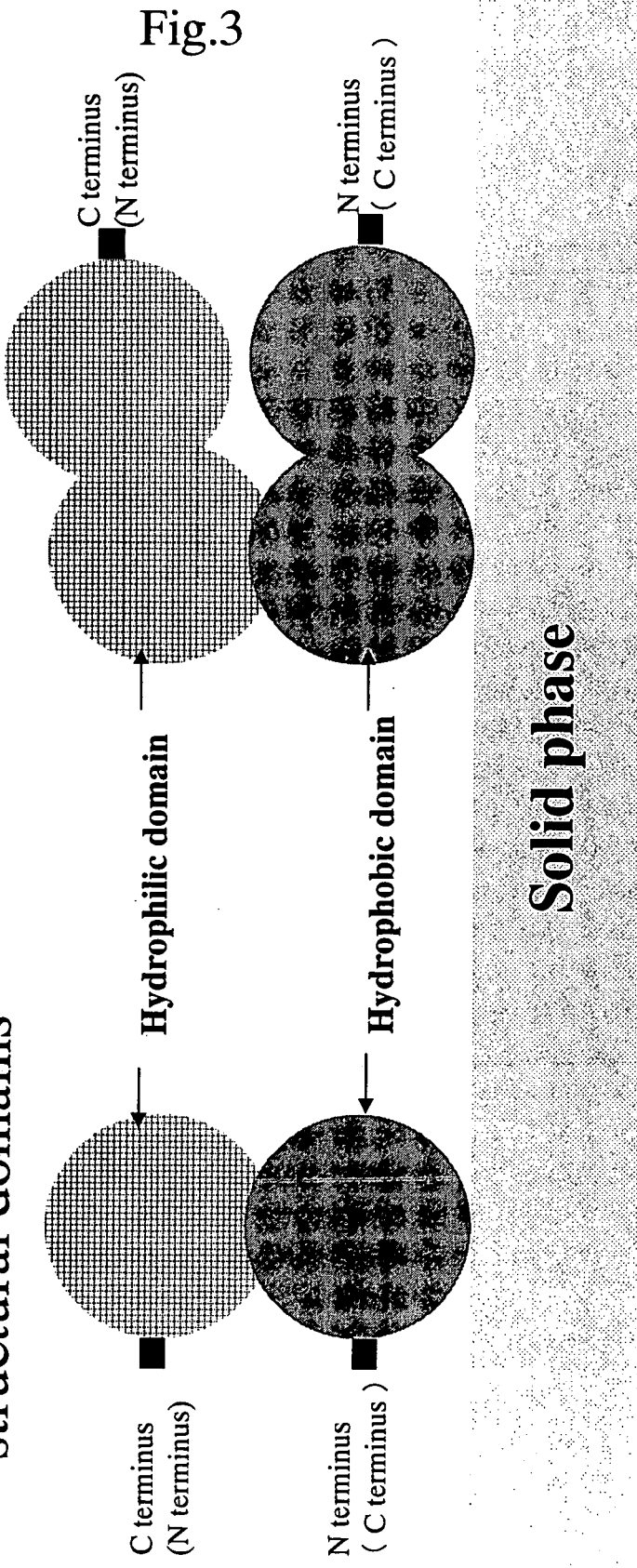
FIG. 3 is a view showing a blocking mechanism of a protein having a blocking ability.

Based on the above, it is speculated that the hydrophobic portion (hydrophobic domain) is absorbed to the material surface and the hydrophilic portion (hydrophilic domain) is hovered over it, and that viewed as whole, the blocking is performed by covering the material surface with the hydrophilic portion. That model is shown in FIG. 3. It is predicted that lipase did not exhibit the blocking ability because lipase was absorbed but the absorbed protein is too hydrophobic and further non-specific absorption to the protein occurred.

For the rate of the hydrophobic portion absorbed to the material surface and the hydrophilic portion which covers the hydrophobic portion, the hydrophilic portion is 0.3 to 10, preferably 0.5 to 5 and more preferably 0.7 to 2 based on 1 of the hydrophobic portion. When the hydrophobic portion is too large, the hydrophilic portion can not cover it, and another protein is further absorbed to the hydrophobic portion absorbed to the material surface. When the hydrophilic portion is too large, an area of the hydrophobic portion absorbed to the material surface becomes too small, the hydrophobic portion can not be sufficiently firmly absorbed and the blocking efficiency is reduced.

In the present invention, "dividing into two" does not mean that the total sequence is divided into about 50% and 50%, and means that the sequence is divided into two of the hydrophobic portion and the hydrophilic portion. When one of or both of the hydrophilic portion and the hydrophobic portion are plurally present, the hydrophilic/hydrophobic rate of the multiple hydrophilic portions/hydrophobic portions is calculated as an average value. The hydrophilic portion and the hydrophobic portion have a clustered portion, preferably a domain structure, respectively. Each portion is 20% or more, preferably 30% or more and more preferably 40% or more of the total sequence. When the structure of the protein is unknown or is difficult to be predicted, it is preferable and effective to analyze by broadly dividing the amino acid sequence into the N terminal side and the C terminal side.

As far as looking at FIG. 14, slight variation in difference of the hydrophilic/hydrophobic rates between the hydrophilic domain and the hydrophobic domain is observed among the proteins, and it seems that only the size of the value is not potentially reflect the blocking ability in detail. One of the factors appears to be a molecular weight. In the present invention, "composed of more than 100 amino acid residues" means that the total number of the amino acid residues in the total amino acid sequence is more than 100. Preferably, the amino acid sequence is composed of more than 150 amino acid residues, and more preferably more than 200 amino acid residues. An upper limit is preferably 2,000 amino acid residues, more preferably 1,500 amino acid residues and still more preferably 1,000 amino acid residue. The hydrophilic portion or domain is composed of preferably 30 or more amino acid residues, more preferably 50 or more amino acid residues, still more preferably 60 or more amino acid residues, particularly preferably 80 or more amino acid residues, and preferably 1,000 or less amino acid residues and more preferably 500 or less amino acid residues.

The hydrophobic portion or domain is composed of preferably 30 or more amino acid residues, more preferably 50 or more amino acid residues, still more preferably 60 or more amino acid residues, particularly preferably 80 or more amino acid residues, and preferably 1,000 or less amino acid residues and more preferably 500 or less amino acid residues.

As used herein, the domain refers to a region having structural or functional one cohesiveness in the molecule, and in the present invention the domain mainly refers to a unit having the structural cohesiveness.

Subsequently, we tried to prove whether this hypothesis is correct or not using a simple protein. A substrate-binding domain of HSP70 (DnaK), one type of heat shock proteins in

Figure 4:
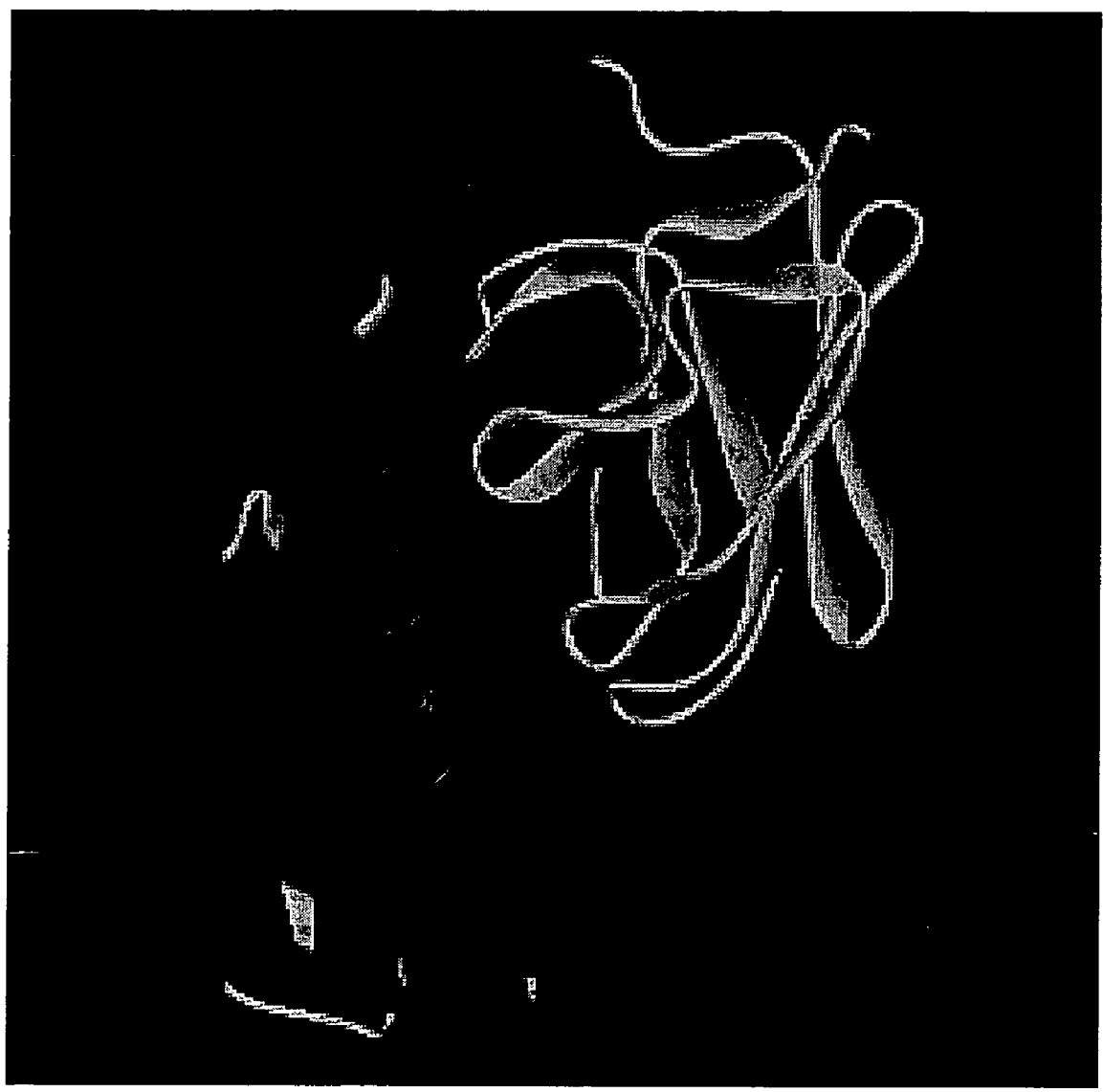
FIG. 4 is a view showing a three dimensional structure of DnaK 384-607. A β-sheet portion and an α-helix portion correspond to an N terminus and a C terminus, respectively.

*Escherichia coli* was used for this experiment. The structure of this protein (DnaK 384-607) has been already demonstrated by NMR analysis (FIG. 4), and it has been found that the protein is composed of two structural regions (domains), i.e., a β sheet region (domain) in the N terminal side and an α helix region (domain) in the C terminal side. It has been also shown by calculation that the hydrophilic/hydrophobic rate is 0.5 in the N terminal side and 0.89 in the C terminal side, and that their difference is 0.39 which is a high value.

First, it was confirmed that this protein (DnaK 384-607) exhibited the blocking ability, consequently the protein was confirmed to have the blocking ability not as good as BSA (FIG. 5), and the availability of the present invention was shown.

Subsequently, various deletion mutants of DnaK 384-607 were made, and it was examined what structure of DnaK played an important role for blocking. The mutants examined this time were shown in FIG. 6. The examined proteins are 6 types of DnaK 384-638, DnaK 384-607, DnaK 384-578, DnaK 384-561, DnaK 508-607 and DnaK 525-607. These proteins can be produced on a large scale using *Escherichia coli* as a host, and it is possible to express by adding a histidine tag to the N terminal side of the protein, easily purify using a nickel chelate column and use for the experiment. In the experiments this time, the protein to which the histidine tag had been added was examined, but since the tag was small, its influence was ignored. Of course, in the case without the tag sequence, it was confirmed that the same result was obtained (Example 7).

Figure 5:
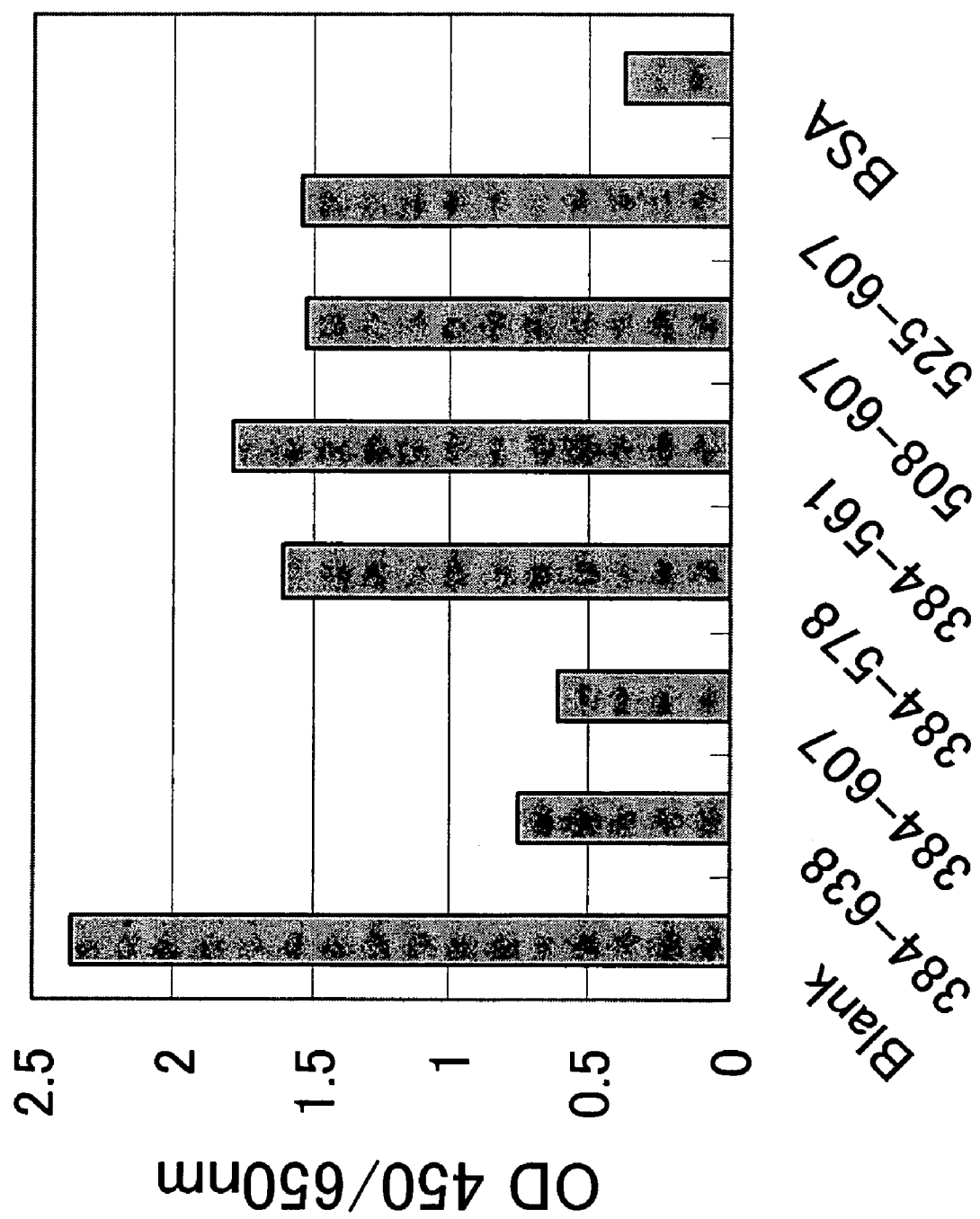
FIG. 5 is a view showing blocking efficiencies of various DnaK mutants.
Figure 7:
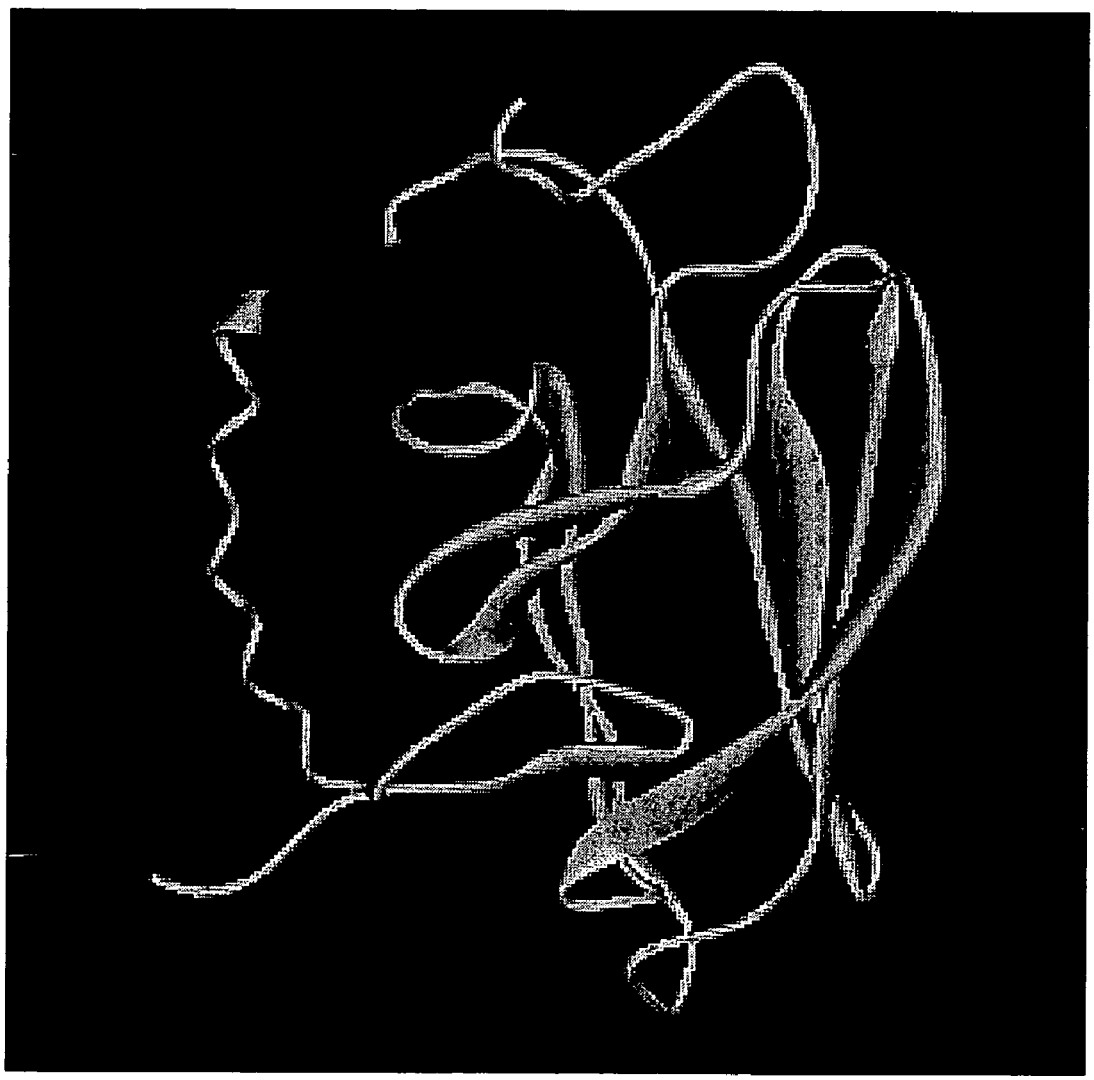
FIG. 7 is a view showing a three dimensional structure of DnaK 381-553.

As a result of the experiment, it was found that the blocking effect was significantly reduced in DnaK 384-578 and DnaK 384-561 obtained by deleting a part of the α helix structure, DnaK 508-607 and DnaK 525-607 obtained by deleting the β sheet portion and seemed to be composed of the α helix structure alone (FIG. 5). Concerning DnaK 384-561, the conformational structure of DnaK 381-553 close thereto has been already shown (FIG. 7), knowing it by analogy, it is predicted that the α helix structure has been broken. The followings are suggested from these. That is, (1) the blocking ability is impaired by reducing or breaking the structure of the hydrophilic portion in the protein having the blocking ability. (2) The hydrophilic portion alone does not exhibit the blocking ability. This seems to be because to exert the blocking ability, the hydrophilic portion is important in addition to the hydrophobic portion and it can be thought that the protein which exhibits the blocking ability exerts the blocking effect by absorbing to the plate by the hydrophobic portion and covering the plate surface with the hydrophilic portion as shown in FIG. 3. It is predicted that this DnaK just corresponds to a left figure in FIG. 3.

Figure 8:
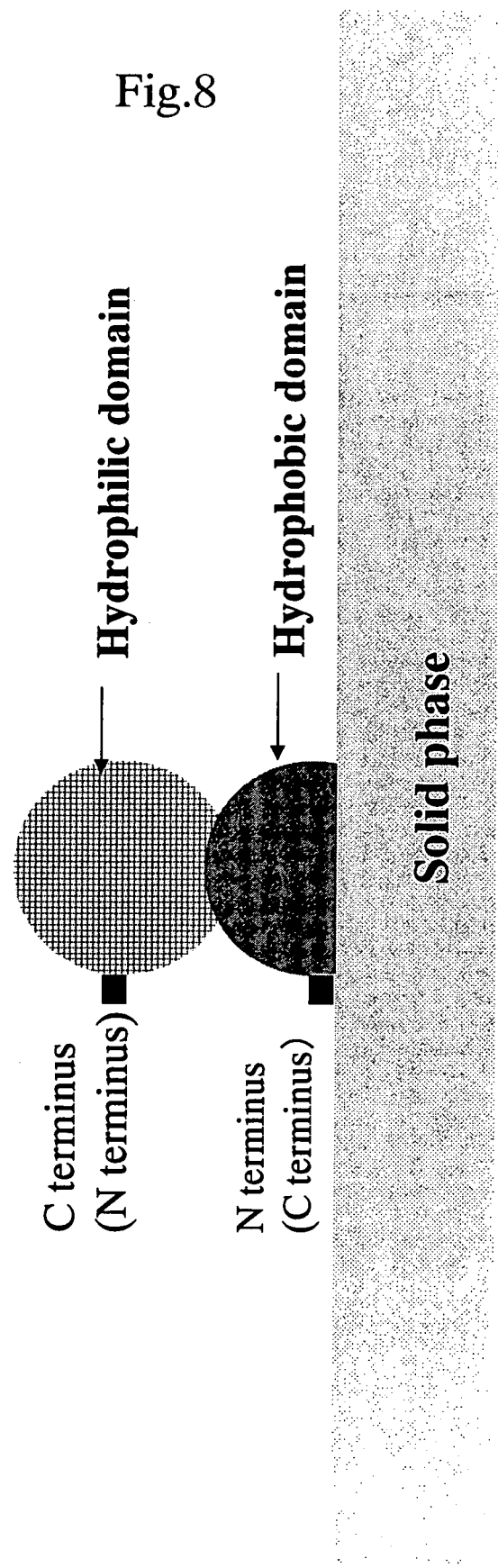
FIG. 8 is a view showing a blocking mechanism of a protein in which a hydrophobic domain was modified.

It is generally known that the hydrophilicity is lost by collapsing a secondary structure by denaturation or mutation. It is predicted that it is not suitable to prepare a partial sequence protein by breaking the hydrophilic domain as also shown from the above examples of DnaK. On the contrary, it seems to be possible to enhance the hydrophobicity by breaking the hydrophobic domain as shown in FIG. 8.

In the present invention, it seems that the domain is important and that at least more than one domain structures are required. Thus, 100 amino acid residues required for composing one structural domain is a rough standard. Therefore, it can be said that it is desirable that the present invention has the domain structure composed of at least more than 100 amino acid residues, i.e., more than one domain structures.

Based on such a fact, the present invention provides a method for screening a novel protein or a novel partial sequence protein for blocking having the blocking ability based on amino acid sequence data. Particularly, the method is the method for screening the protein or the partial sequence protein which meets the conditions shown below.

A) The amino acid sequence is divided into two, and an absolute value of a difference between hydrophilic/hydrophobic rates in divided two portions is 0.1 or more, calculated using the following formula from content rates of hydrophilic amino acids (D, E, K, H, R, Y) and hydrophobic amino acids (G, A, V, L, I, M, F, W, P); [Hydrophilic/hydrophobic rate]=[Content rate of hydrophilic amino acids]/[Content rate of hydrophobic amino acids].

B) The hydrophilic portion (in higher value of hydrophilic/hydrophobic rate) is 0.5 or more.

C) The protein is composed of more than 100 amino acid residues.

In the above conditions, D is aspartic acid, E is glutamic acid, K is lysine, H is histidine, R is arginine, Y is tyrosine, G is glycine, A is alanine, V is valine, L is leucine, I is isoleucine, M is methionine, F is phenylalanine, W is tryptophan and P is proline. The hydrophilic amino acid and the hydrophobic amino acid are variously defined depending on textbooks. In the present invention, the hydrophilic amino acids were aspartic acid, glutamic acid, lysine, histidine, arginine and tyrosine. Also the hydrophobic amino acids were glycine, alanine, valine, leucine, isoleucine, methionine, phenylalanine, tryptophan and proline.

The partial sequence protein referred to herein indicates the protein composed of the partial amino acid sequence of the wild type protein and is preferably the protein having more than one domain structures.

When the amino acid sequence is divided into two of the N terminal side and the C terminal side, it is not necessarily required to precisely divide into two, but it is preferable to divide so that the numbers of the amino acid residues in both are almost equal as possible. When the signal peptide is predicted from the amino acid sequence, it is better to calculate by excluding that portion. In fact, in the present invention, in all of BSA, α-casein and lipase, the calculation was performed using the mature type of the amino acid sequence where the signal peptide had been removed.

Division methods as shown in FIG. 2 other than the method of dividing into two of the N terminal side and the C terminal side are preferably used. In such a case, such a method can be preferably applied to the protein whose conformational structure has been demonstrated or predicted.

To calculate the amino acid contents from the amino acid primary sequence, it is effective to use software for analyzing gene/amino acid sequences. The analysis software is not particularly limited, and in the present invention, the analysis was performed using GENETYX (software development company).

It is also effective for efficiently performing screening works to make the hydrophilicity and the hydrophobicity of the protein graphs using a hydrophobicity calculation function of the software. Preferably, a calculation formula of hopp & woods is used.

The present invention is the protein or the partial sequence protein having the blocking ability, screened from the amino acid sequence by the above method, and the protein or the partial sequence protein which is obtained by the following analysis step D and meets the condition E.

D) 1. A step of adding a candidate protein (50 to 100 mg/mL, diluted with 20 mM Tris-HCl, pH 7.0) which meets the conditions of claim 1 and bovine serum albumin (fraction V) prepared by the same way to wells of a polystyrene immunotiter plate, blocking at 2 to 10° C. for 4 to 5 hours and removing a liquid.

2. A step of adding normal human serum diluted 25 to 100 times with PBS(−), leaving stand at 37° C. for one hours, and subsequently washing the plate with PBS(−) (0.05% Tween® (polysorbate)20).
3. A step of comparing IgG amounts non-specifically absorbed to the plate using an enzyme-labeled anti-human IgG antibody by a calorimetric method using a chromogenic substrate.

E) A developed color intensity for the candidate protein is 2.5 times or less, preferably 2 times or less, more preferably 1.5 times or less, still more preferably 1.2 times or less and especially 1 time or less of the developed color intensity for bovine serum albumin.

Herein, the blocking ability is measured by making non-specific absorption of human serum IgG known for non-specific absorption to the plastic plate a rough standard. As used herein, the polystyrene immunotiter plate (96-well type) refers to an immunotiter plate of 96-well type made from polystyrene, generally used in immunoassays. A candidate protein purified by an appropriate method is used, and finally diluted to 50 to 100 mg/mL with 20 mM Tris-HCl (pH 7.0). Simultaneously, bovine serum albumin (BSA) is similarly prepared. As BSA, Fraction V commercially available from Sigma can be used. BSA need not always be Fraction V as long as it has the same performance. The blocking is performed at 2 to 8° C. for 4 to 5 hours, and subsequently the solution is completely removed to progress to next step without washing.

The human serum used herein is not particularly limited as long as it is the serum isolated from a normal adult. Since the undiluted serum is at high concentration, it is better to dilute 25 to 50 times with PBS to use. Since the amount of serum IgG is different in individuals, a dilution rate may be slightly changed. The non-specific absorption to the plate is performed at 37° C. for 30 minutes. In order to precisely measure, it is preferable that the amount of the serum added at this time is smaller than that of the solution used for the first blocking. For example, when 100 μL is used for the blocking, 50 μL of a diluted serum solution is added. Finally, after reacting precisely for one hour, the solution is removed, and the plate is washed with the sufficient amount of 0.05% TWEEN® (polysorbate) 20/PBS(−). It is preferable to wash three times, and more preferably four times. Washing may be performed using a plate washer for exclusive use.

Subsequently, an anti-human IgG antibody labeled with an enzyme is diluted with an appropriate solution to an appropriate concentration, and added to the above wells. It is suitable to react at 37° C. for one hour. It is preferable to dilute the antibody to a level at which an ordinary immunological detection is performed, and to use the solution containing a suitable blocking agent (BSA or casein) for the dilution of the antibody because no variation is shown. More preferably, it is better to use 0.01 M phosphate buffer (pH 7.4) containing 0.15 M NaCl and 0.5% casein. As the enzyme used for labeling, peroxidase and alkali phosphatase are preferably used, and in particular, peroxidase is preferably used. As a color development reagent for peroxidase, 3,3'5,5'-tetramethylbenzidine (TMBZ) is preferably used. As a color development substrate for alkali phosphatase, WT-1 can be used. It is desirable that a time period for color development is in the range at which an absorbance in the target well is quantitative (0.5 to 1.5). Note because no correct value is obtained when the absorbance exceeds the quantitative range. No correct value is obtained when the plate is dried throughout all manipulation.

The lower the value obtained in this way is, it indicates the higher blocking efficiency. In the present invention, it was determined that a sample had the blocking ability when the sample exhibited the value which was 2.5 times or less than the value of BSA. Therefore, the novel protein or the novel partial sequence protein for blocking of the present invention is the protein which meets the conditions shown in claim 1 and exhibits the value 2.5 times or less than the value of BSA in this assay, i.e., having the blocking ability.

As an alternative method of this assay, it is also possible to use the method shown in Example 7. That is, serially diluted peroxidase is added to the candidate protein solution, which is then subjected to a solid phase to absorb for a certain time period, and subsequently the non-specific absorption of peroxidase is measured. The absorbed peroxidase is confirmed as with the above method using the color development method of 3,3',5,5'-tetramethylbenzidine. Also in this assay, it is an indicator showing the blocking ability to exhibit the value 2.5 times or less than the value of BSA. Likewise, the diluted peroxidase solution may be added to the solid phase previously blocked, and its non-specific absorption may be measured. In that case, it is also the indicator showing the blocking ability to exhibit the value 2.5 times or less than the value of BSA. The concentration of the peroxidase solution used herein is preferably 0.05 mg/mL, but it is conductive to the correct evaluation to control and use so as to measure in the commonsense range. The dilution of peroxidase is preferably performed using PBS(−), but is not particularly limited.

From the above, it can be said that it is preferable that the present invention has more than one domain structures, but as this example, especially for the hydrophobic domain, a part of the domain structure of one in two domains may be lacked. It is preferable that the number of the amino acid residues in the protein or the partial sequence protein of the present invention is 100 or more, preferably 150 or more and more preferably 180 or more.

Furthermore, the present invention is the novel protein achieving the improved blocking efficiency of the protein or the partial sequence protein by modifying the amino acid sequence of the protein which meets the conditions of the above claim 1. The "novel" referred to herein is the "novel" at the level of amino acid modification, and the novel protein may be the already known protein. In the case of the partial sequence, those having the partial sequence unknown so far are regarded as the novel proteins.

In the present invention, the amino acid sequence may be modified by any of or a combination of substitution, deletion, and insertion. For directionality of mutation, the mutation to further enhance the hydrophobicity in the hydrophobic region or the mutation to further enhance the hydrophilicity in the hydrophilic region are effective, and suitably used. The deletion and the insertion of the amino acid sequence are effective in order to change the conformational structure of the protein, it is thought that the hydrophobic region hidden by the hydrophilic region is exposed on the protein surface. Meanwhile, as shown in the above example, it can be said that the amino acid modification to break the hydrophilic domain structure is not preferable.

The modified protein may be derived from the prokaryotic organism or the eukaryotic organism. Considering the mass production using *Escherichia coli*, the protein derived from the prokaryotic organism is preferably used. More preferably, the protein derived from *Escherichia coli* is used. The protein used may be a partial structure such as domain, which is rather preferably used.

In particular, the blocking agent is often used as a stabilizing agent and an excipient by combining with an enzyme in some cases, and it can be said that the protein which does not have a particular function of an enzymatic activity is suitable for the present invention. The protein from which the domain having the enzymatic activity has been deleted is preferably used.

In the present invention, the protein derived from HSP70 family protein is preferably used. More preferably the protein derived from the DnaK protein of *Escherichia coli* is used. Preferably, a substrate-binding domain of the HSP 70 family protein from which an ATPase domain has been deleted is preferably used, and more preferably, the substrate-binding domain of the DnaK protein of *Escherichia coli* from which an ATPase domain has been deleted is used. The substrate-binding domain of the DnaK protein was already introduced above as Example.

The protein belonging to the HSP70 family used for the present invention is not particularly limited, and is selected from DnaK in *Escherichia coli*, Ssalp present in yeast cytoplasm, Ssclp present in yeast mitochondria, Kar2p present in yeast endoplasmic reticulum, HSP70 present in mammalian cytoplasm, Bip present in mammalian endoplasmic reticulum, mHsp70 present in mammalian mitochondria and HSC70 which is constitutively expressed regardless of the presence or absence of heat shock and is a homolog of HSP70, and the like. Many homologs are known in the HSP 70 family, and the above ones are parts of them. Of course, it is possible to easily predict that the same effect can be expected for homologs other than those listed above.

Figure 6:
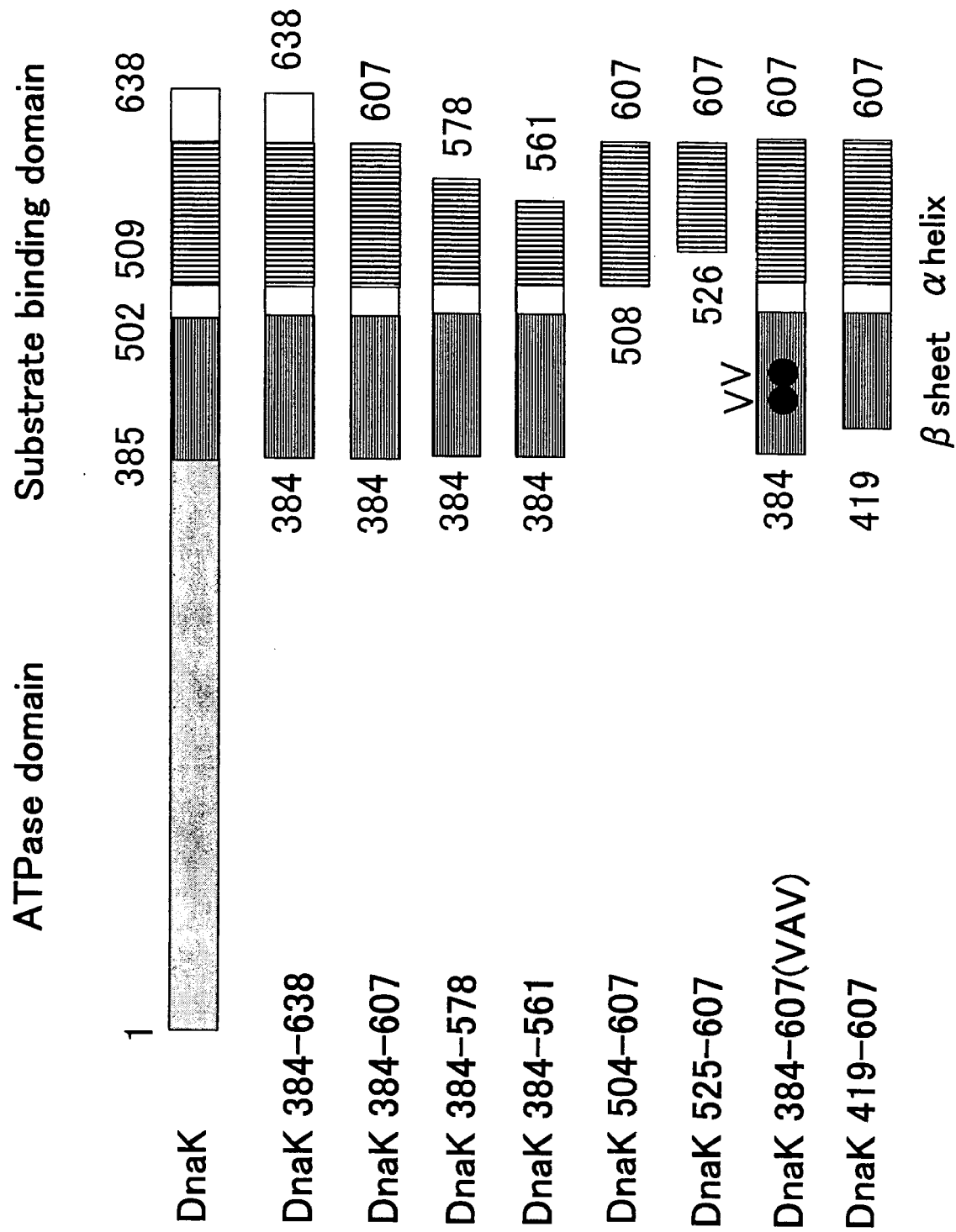
FIG. 6 is a view showing structures of an *Escherichia coli* DnaK protein and produced mutants thereof.

In particular DnaK in *Escherichia coli* has been well-studied, and thus, it can be said that it is relatively easy to predict the effect of the amino acid modification. This protein is composed of 638 amino acid residues, and comprised of an "ATPase (ATP-binding) domain" composed of the amino acids at positions 1 to 385 and a "substrate-binding domain" composed of the amino acids at positions 386 to 638 (FIG. 6). The sequence of the DnaK protein is shown in SEQ ID NO:1, and its gene sequence is shown in SEQ ID NO:2. HSP70 has been known to bind to a newly formed polypeptide and a partially folded protein and help refolding of the protein which can not fold spontaneously. It is also known that HSP 70 recognizes abundant substrates because it works in a relatively early phase of protein synthesis.

It is also known that the substrate-binding domain itself of DnaK has an action to persuade the refolding of the denatured protein (Proc. Natl. Acad. Sci. USA, 99:15398-15403, 2002), and it is thought that it is possible to develop various intended uses by the use of this molecule.

When achieving the present invention, we focused this substrate-binding domain of DnaK, and could obtain various findings for expression mechanism of blocking action by various examinations to complete the present invention.

Figure 9:
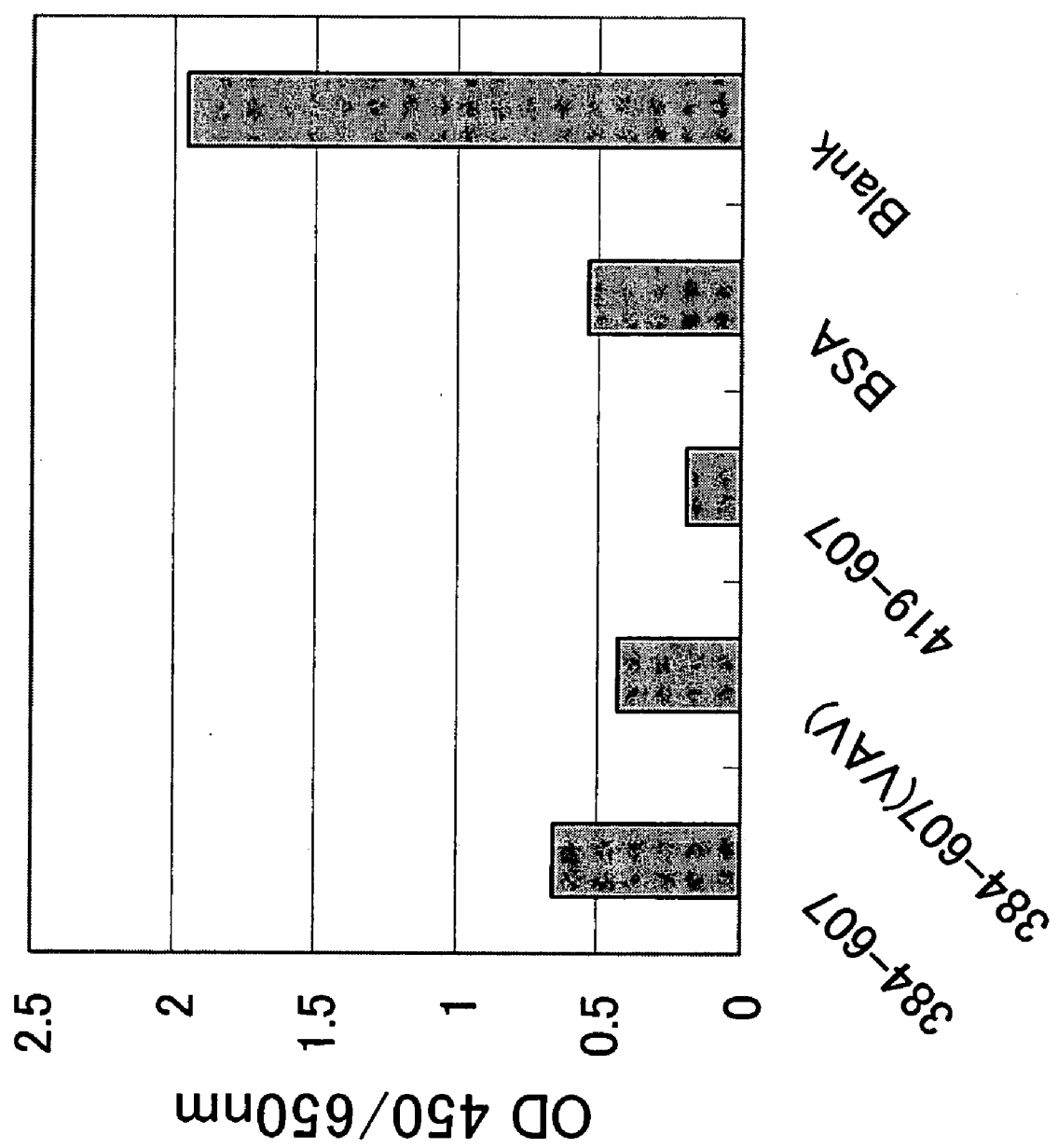
FIG. 9 is a view showing blocking efficiencies of various DnaK mutants.

First, we attempted to make the protein excellent in blocking efficiency by adding the mutation to a β sheet structure portion to enhance the hydrophobicity in the β sheet portion. The attempt is that (1) a more hydrophobic portion of the β sheet is exposed by deleting a part of the N terminus of the β sheet (the β sheet structure is broken to enhance the hydrophobicity) and (2) a hydrophilic amino acid in the β sheet is substituted with a hydrophobic amino acid. As a result, remarkable enhancement of the blocking efficiency could be observed in DnaK 419-607 where the N terminal portion of the β sheet structure had been deleted and DnaK 384-607 (D479V, D481V) where the hydrophilic amino acid had been substituted with the hydrophobic amino acid (FIG. 9). This time especially, the remarkable enhancement of the blocking efficiency was observed in DnaK 419-607. It appears that this protein exhibits the blocking in a form shown in FIG. 8. That is, it is thought that by changing the structure of the hydrophobic domain, the structure of the hydrophobic domain was changed to enhance the hydrophobicity of the hydrophobic domain, which was conductive to the enhancement of the blocking ability.

The enhancement of the blocking ability referred to in the present invention indicates that the blocking ability is further enhanced compared to that of the original protein and protein partial sequence by giving amino acid substitution, deletion and insertion to the candidate protein.

This enhancement of the blocking ability is preferably measured by the method shown in claim 2. The enhancement of the blocking ability includes the enhancement of the blocking ability for a long time period and a short time period, and the blocking ability may be enhanced in either one or both.

Discussing the reason why the efficiency was remarkable in DnaK 419-607 in more detail, it is speculated that the efficiency is caused by exposing outside a part of an inside of a horseshoe shaped structure which is hydrophobicity-rich for trapping a peptide as a substrate of a chaperone by removing the β sheet portion adjacent to a hinge portion of the horseshoe shaped structure of the DnaK substrate-binding domain.

That is, the present invention is the DnaK protein whose blocking efficiency has been improved, characterized by deleting the amino acid sequence from the N terminus to at least position 387 and at most position 472. The present invention is also the DnaK protein whose blocking efficiency has been improved, characterized by deleting the amino acid sequence from the N terminus to at least position 387 and at most position 418. More preferably, the present invention is the protein composed of the amino acid sequence at positions 419 to 607 in the DnaK protein.

The present invention is the protein whose blocking efficiency has been improved, characterized in that the hydrophilic amino acids of a part of the DnaK protein where the ATPase domain or a part thereof has been deleted are substituted with the hydrophobic amino acids. More particularly, the present invention is the protein where the amino acid sequence in the part of the DnaK protein has been deleted by deleting the ATPase domain or the part thereof, the protein where the blocking efficiency has been improved by substituting aspartic acid at positions 479 and 481 with valine. More preferably, the protein composed of the amino acid sequence at positions 384 to 607 in the DnaK protein where aspartic acid at positions 479 and 481 have been substituted with valine is used.

The modification referred to in the present invention indicates that the amino acid sequence has been modified by amino acid substitution, deletion and insertion in the candidate protein. For this modification, it is preferable to modify the amino acid by intending so that (1) the hydrophilic domain is not broken and (2) the hydrophobic domain is made more hydrophobic, based on the above discussion after selecting the partial sequence of the candidate protein or the protein. Although it is not shown in the present invention, it should be of course considered to make the hydrophilic domain more hydrophilic.

In the present invention, a blocking speed was also examined, and usefulness of the present invention was shown. That is, the blocking efficiency was measured when blocked for 5, 10, 30 minutes and 3 hours. As a result, it was found that DnaK 419-607 whose effect was the most remarkable had the blocking efficiency of 87.5% whereas DnaK 384-638 had the blocking efficiency of 58.8% in blocking for 5 minutes. This speed is fast even compared with BSA which shows the equivalent effect after 3 hours, and it is predicted that DnaK 419-607 is absorbed to the polystyrene plate to exert the blocking effect at a very early stage. Therefore, by the use of this invention, it seems that it is possible to develop a novel blocking agent having a performance equivalent or more than that of conventional BSA.

The present invention is the protein for blocking having one or more hydrophilic domains and one or more hydrophobic domains, and the protein for blocking where the hydrophobic domain can be absorbed to the material surface and the hydrophilic domain can cover the hydrophobic domain absorbed to the material surface. The domain referred to herein is preferably a structural amino acid cluster composed of 50 or more amino acids, and those partially deleted or added are regarded as the domain.

The present invention also defines the blocking speed. That is, the present invention is the modified protein characterized in that the blocking speed is enhanced compared with that of BSA. Particularly, the present invention is also the modified protein characterized in that the blocking ability for less than 10 minutes is more excellent than that of BSA under the condition where the protein amounts have been adjusted so that the blocking efficiency equivalent to that of BSA is exhibited in blocking for 3 hours. The modification herein indicates that a gene sequence encoding the protein of a wild type has been converted by amino acid substitution, deletion and insertion. An evaluation method is not particularly limited, methods shown in Examples 5 and 7 are preferably used, and the blocking is measured using non-specific absorption of IgG or peroxidase to the polystyrene plate as the indicator. In the evaluation method using IgG, the blocking is performed for 1 to 10 minutes, preferably 2 to 10 minutes, subsequently human serum diluted with PBS(-) is added, then washing is performed, an anti-human IgG antibody at an optimal concentration is reacted, subsequently washing is performed, and then the amount of non-specifically absorbed IgG is measured by absorbance of colored products from TMBZ. Also in the evaluation method using peroxidase, first, horseradish peroxidase for labeling (supplied from Toyobo Co., Ltd., PEO-131) is dissolved at 2 mg/mL in the protein solution whose blocking ability is to be measured. Then serial dilutions of 40 to 320 times of the peroxidase solutions are made from the above solution, and 100 μL of each dilution is dispensed in a polystyrene 96-well microplate. The plate is left stand at room temperature for one hour, subsequently the solution is removed, and the plate is washed with PBS buffer containing 0.02% TWEEN® (polysorbate) 20. This washing manipulation is repeated six times, and then the washing solution is thoroughly removed. Tetramethylbenzidine solution is added, the plate is incubated at 37° C. precisely for 10 minutes, and then 1N sulfuric acid is added to stop the reaction and develop the color. This absorbance is measured by a microplate reader at a major wavelength of 450 nm and minor wavelength of 650 nm. Details will be described in Example 7. Likewise, the diluted peroxidase solution may be added to the solid phase previously blocked, and its non-specific absorption may be measured. The concentration of the peroxidase solution used herein is preferably 0.05 mg/mL, but it conductive to the correct evaluation to control and use so as to measure in the commonsense range. The dilution of peroxidase is preferably performed using PBS(-), but is not particularly limited.

In this Example, as BSA which exhibits the blocking ability equivalent to that of 0.7 mg/mL of DnaK 419-607 after 3 hours, 2.4 mL/mL of BSA (Fraction V, supplied from Sigma, code: A-4503) was used (the protein amount was measurement by Bradford method). The amount of the specimen protein may be in the commonsense range for measuring the blocking ability, and is preferably used in the range of 0.5 to 1 mg/mL. The concentration of BSA used for this measurement is the amount at which the blocking efficiency equivalent to that of the specimen protein after 3 hours is exhibited, and this requires the previous examination of the concentration. As the buffer which dissolves those proteins, 20 mM Tris-HCl (pH 7.0) and PBS(-) are preferably used, but the buffer is not particularly limited.

The protein or a protein fragment used for the present invention may have a tag, and in fact, the examination was performed using those where a histidine tag had been added to the amino terminus. As the tag, any of a histidine tag, a GST (glutathione S-transferase) tag, a MBP (maltose binding protein) tag, a Flag tag, a Myc tag, and a TAP (tandem affinity purification) tag may be used, and may be used by fusing an optional protein as needed. An optional amino acid sequence may be added to the known tag.

Further more, it is a matter of course, and the tag unknown generally or the optional amino acid sequence may be added. Concretely, when the partial sequence of the protein whose N terminal side has been deleted is used, it is of course necessary to introduce a methionine residue to the N terminus. Also considering the expression enhancement or the relation with restriction enzyme sites, the addition of several amino acids is also thought. For example, four amino acids of MRGS have been added to the N terminus of DnaK 419-607N in Example 7. Of course, the protein may be expressed as a fusion protein with an optional protein. The position of addition may be the N terminal side or the C terminal side.

An expression method of the present protein is not particularly limited, but the method of expressing using a prokaryotic organism is preferable and furthermore the method of expressing using *Escherichia coli* is more preferable. An expression vector is not particularly limited, and those generally used for the expression may be used.

Concerning the method of purifying the protein of the present invention, the protein can be efficiently purified in some cases by heating a crude purification solution at an appropriate temperature and purifying its centrifugation supernatant, in addition to the method of purifying using the above tag. The heating is performed preferably at 50° C. or above and more preferably 70° C. or above. The substrate-binding domain of DnaK used this time has heat resistance, no aggregation is observed under the condition at 70° C. for 30 minutes, and it has been confirmed that the protein remains in the centrifugation supernatant fraction. Therefore, when purified, the protein can be easily purified by purifying this heated centrifugation supernatant on column chromatography, and it is very economical. It can be also anticipated that co-existing enzymes are deactivated by passing through the heating step.

Figure 12:
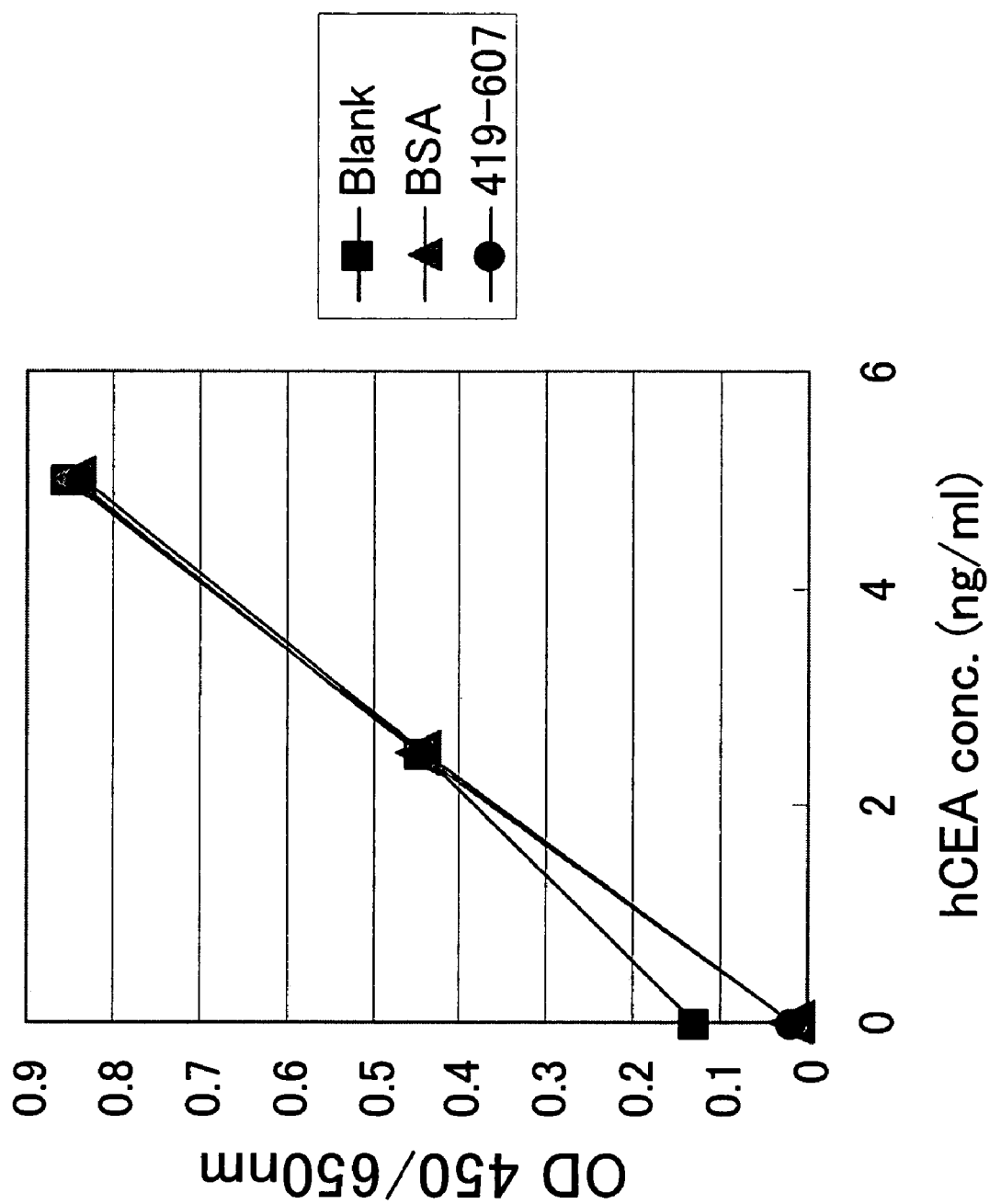
FIG. 12 is a view showing practical application of the DnaK mutant to blocking in ELISA.

The protein of the present invention whose blocking efficiency has been improved can be practically applied to blocking agents, excipients, stabilizing agents, refolding aids, coating agents for cell attachment and coating agents for medical use. In particular, the protein is greatly expected as the blocking agent in detection systems which take advantage of immune reactions. It is predicted that it is possible to use for ELISA, immunohistological staining and Western blotting. In fact, when the present invention was completed, a potential application to ELISA (enzyme-linked immunosorbent assay) was examined and actual good results were obtained (FIG. 12).

One embodiment of the present invention is the blocking agent, the excipient, the stabilizing agent or the refolding aid containing DnaK 419-607.

One embodiment of the present invention is the blocking agent, the excipient, the stabilizing agent or the refolding aid containing DnaK 384-607 (D479V, D481V).

The effects of the present invention will be made more clearly by exemplifying Examples of the present invention.

EXAMPLE 1

Screening of Candidate Proteins

Candidate proteins were screened from amino acid sequences using mainly a nucleic acid/amino acid sequence analysis software: GENETYX (software development company). This software has a function to calculate the numbers of hydrophilic amino acid residues and hydrophobic amino acid residues from a primary sequence of the amino acids, and was convenient. The numbers of the hydrophilic amino acids and the hydrophobic amino acids contained in the sequences of an N terminal side half and a C terminal side half of the proteins found to exhibit various blocking ability, the proteins derived from *Escherichia coli* or the partial sequence thereof were calculated by GENETYX, and hydrophilic amino acid content rates, hydrophobic amino acid content rates, hydrophilic/hydrophobic rates and absolute values of differences of the hydrophilic/hydrophobic rates between divided two are collectively shown in FIGS. 13 and 14. In accordance with the definition of GENETYX herein, the hydrophilic amino acids were aspartic acid, glutamic acid, lysine, histidine, arginine and tyrosine. The hydrophobic amino acids were glycine, alanine, valine, leucine, isoleucine, methionine, phenylalanine, tryptophan and proline.

EXAMPLE 2

Cloning and Expression of DnaK Fragments

A DnaK fragment was cloned by amplifying an objective gene fragment using PCR method with genomic DNA extracted from *Escherichia coli* K-12 strain as a template. KOD-Plus-supplied from Toyobo Co., Ltd. was used for PCR amplification of the gene. Concretely, in the amplification of DnaK 384-638, a sample was prepared to contain reaction buffer, 1 mM $MgSO_4$, 15 pmole primers shown in SEQ ID NOS:3 and 4, 1 unit of polymerase and 100 ng of *Escherichia coli* DNA in 50 µL of a reaction solution, and subjected to the reaction of 25 cycles at 94° C. for 15 seconds, 55° C. for 30 seconds and 68° C. for one minute after the reaction at 94° C. for 2 minutes. An amplified DNA fragment was digested with a restriction enzyme BamHI, and cloned into a BamHI-SmaI site of pQE30 (the DNA fragment amplified using KOD-Plus-(supplied from TOYOBO) had a blunt end, and thus a downstream side of the amplified fragment was directly used). The sequence of the cloned gene was confirmed by sequencing analysis. A 6×His sequence (histidine tag) can be added to the N terminus of the objective protein by cloning into this vector. An expression plasmid, pQE-DnaK 384-638 was made in this way.

Expression and purification of the protein were performed using a supernatant obtained by culturing JM109 in which the gene had been introduced in LB medium with shaking for 16 hours, collecting microbial cells by centrifugation, suspending the microbial cells in 20 mM Tris-HCl (pH 7.0), to which sonication was then given, and subsequently centrifuging by high speed microcentrifuge. Concretely, the protein was purified using His-Select HC Nickel Affinity Gel (supplied from Sigma), and was finally dialyzed overnight against 20 mM Tris-HCl (pH 7.0) to use for experiments. The protein concentration was measured by Bradford method (Bio-Rad Protein Assay Kit: 500-0006, supplied from Bio-Rad) using BSA as the standard.

EXAMPLE 3

Preparation of C Terminus-Deleted DnaK Clone and Point Mutant

C terminus-deleted DnaK clones were made by using pQE-DnaK 384-638 made in Example 2 as the template and introducing a stop codon at an optional position using Quick-Change method. Actually, the clones were made using QuickChange site directive mutagenesis kit (supplied from Stratagene) in accordance with instructions thereof. The produced clones and the combination of the primers used are as follows. DnaK 384-607: SEQ ID NOS:5 and 6, DnaK 384-578: SEQ ID NOS:7 and 8, and DnaK 384-561: SEQ ID NOS:9 and 10. For DnaK 384-607 (D479V, D481V), mutations were introduced using pQE-DnaK 384-607 as the template and SEQ ID NOS:11 and 12. The sequence of each mutant was confirmed by sequencing analysis, and subsequently the protein was purified in accordance with the method described in Example 2.

EXAMPLE 4

Preparation of N Terminus-Deleted DnaK Clones

The PCR amplification was performed using pQE-DnaK 384-607 produced in Example 2 as the template and the primers shown below, and an amplified fragment was introduced into the BamHI-SmaI site of the pQE30 vector in accordance with the method in Example 2. The produced clones and sets of the primers are as follows. DnaK 508-607: SEQ ID NOS:13 and 4, DnaK 525-607: SEQ ID NOS:14 and 4, and DnaK 419-607: SEQ ID NOS:15 and 4. The sequence of each mutant produced was confirmed by sequencing analysis, and subsequently the protein was purified in accordance with the method described in Example 2.

EXAMPLE 5

Blocking Effect

The blocking efficiency was measured using the following method.

The examination was performed by making non-specific absorption of human serum IgG to a polystyrene plate an indicator.

As the method, 100 µL of BSA (Fragment V, supplied from Sigma) and various DnaK samples diluted with 20 mM Tris-HCl (pH 7.0) were added to a polystyrene 96-well immunoplate (E.I.A./R.I.A. 8 Well Strip, supplied from Costar), left stand at 4° C. for 4 hours (basically the plate was left stand for 4 hours, but when blocking time periods were examined, optional time periods were set.). Subsequently, the solution was removed from the plate, then 50 µL of normal human serum diluted with PBS(-) 50 times was added, and incubated at 37° C. for one hour. Subsequently, each well was washed four times with 200 µL of a washing solution (PBS (-), 0.05% TWEEN® (polysorbate) 20), 50 µL of a peroxidase-labeled anti-human IgG antibody (supplied from Jackson ImmunoResearch) diluted with an antibody dilution (0.01 M PB (pH 7.4), 0.15 M NaCl, 0.5% casein) to an optimal concentration was added to each well, and incubated at 37° C. for one hour. Subsequently, each well was washed four times with 200 μL of the washing solution (PBS(−), 0.05% TWEEN® (polysorbate)20), 100 μL of a color development reagent (3,3',5,5'-tetramethylbenzidine, TMBZ) was added to allow color development at room temperature for 5 minutes, and then 50 μL of 1N sulfuric acid was added to stop the reaction. The color development was measured using an ELISA reader at a major wavelength of 450 nm and a minor wavelength of 650 nm. The Bradford method was used for quantification of the protein.

First, the blocking efficiency for 4 hours was measured for BSA, DnaK 384-638, DnaK 384-607, DnaK 384-578, DnaK 508-607 and DnaK 525-607 prepared at 0.7 mg/mL. Consequently as shown in FIG. 5, those other than BSA, DnaK 384-638 and DnaK 384-607 exhibited the low blocking effect. In the clines which exhibited the low blocking effect, DnaK 384-607 and DnaK 384-578 are the clones where the α helix was deleted whereas DnaK 508-607 and DnaK 525-607 are the clones where the β sheet was deleted. Therefore, it has been speculated that the blocking using the substrate-binding domain of DnaK requires both the α helix structure and the β sheet structure.

Subsequently, the blocking effect for 4 hours was compared in DnaK 384-607 (D479V, D481V) and DnaK 419-607 (each 0.7 mg/mL) made for the purpose of enhancing the hydrophobicity of the β sheet using BSA and DnaK 384-607 at the same concentration as controls. As a result, both DnaK 384-607 (D479V, D481V) and DnaK 419-607 exhibited higher blocking efficiency than BSA at the same concentration, and in particular the effect was remarkable in DnaK 419-607 (FIG. 9).

Figure 10:
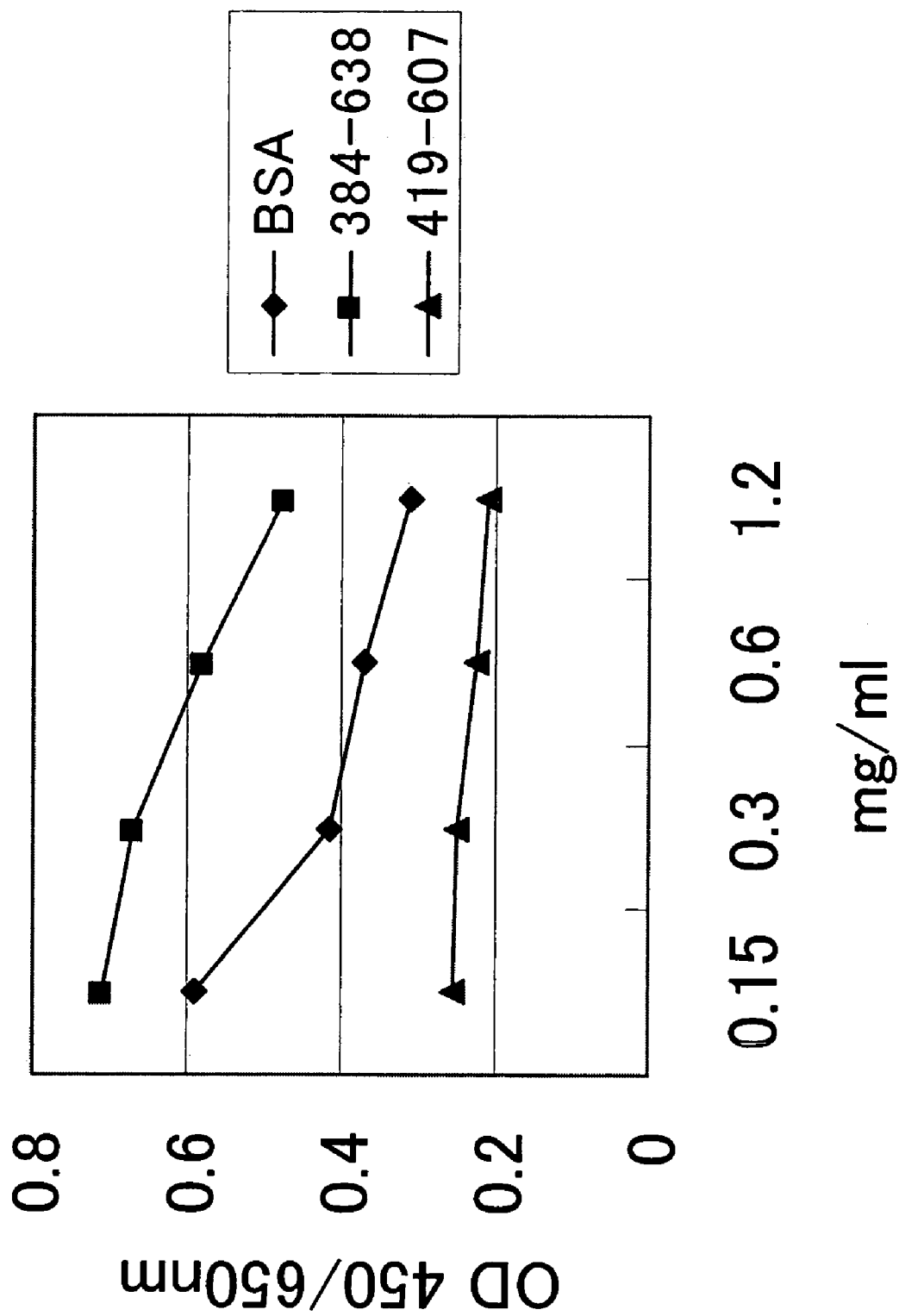
FIG. 10 is a view showing a correlation of DnaK mutant concentrations and blocking effects.

Furthermore, blocking concentrations and the blocking effect in the blocking for 4 hours were examined for DnaK 419-607 which had the highest effect in the above experiment, DnaK 384-638 and BSA. As a result, 0.15 mg of DnaK 419-607 had more remarkable effect than 12 mg of BSA, and DnaK 419-607 was suggested to be capable of being used as the blocking agent at very low concentrations (FIG. 10).

Figure 11:
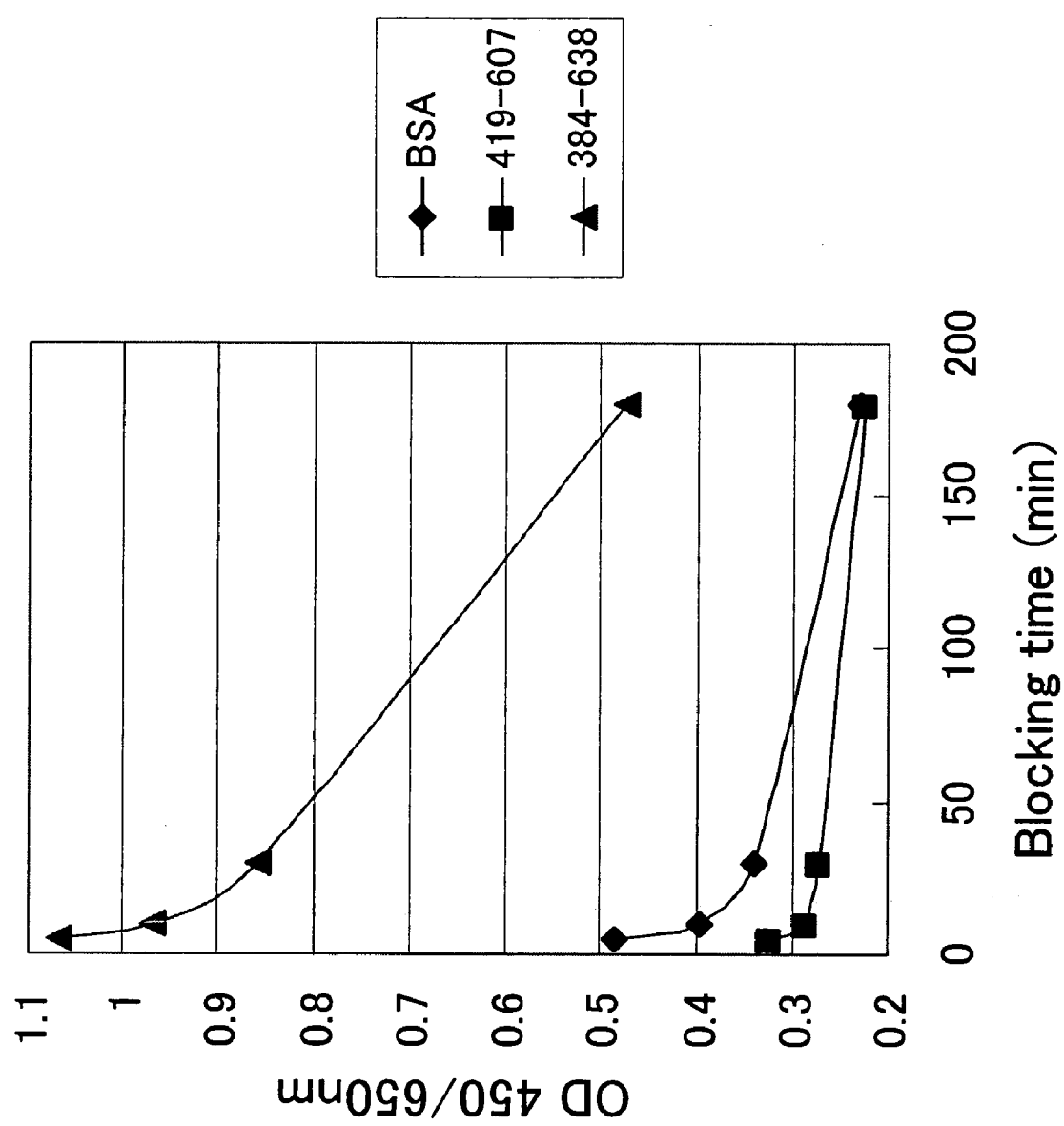
FIG. 11 is a view showing blocking speeds of DnaK mutants.

Finally, the blocking time period and the blocking effect were examined for DnaK 419-607 which had the highest effect in the above experiment, DnaK 384-638 and BSA. The protein concentration was 0.7 mg/mL for DnaK 419-607 and DnaK 384-638, and was 2.4 mg/mL for BSA, at which BSA exhibited the effect equivalent to 0.7 mg of DnaK 416-607 in the above examination. As a result, it was found that the time period required for the blocking by DnaK 419-607 was dramatically short and the sufficiently effective blocking effect was obtained, and that DnaK 419-607 exhibited the blocking effect more early than BSA at 2.4 mg/mL which exhibited the equivalent effect after 3 hours (FIG. 11).

EXAMPLE 6

Blocking Effect (ELISA)

Usefulness of the DnaK fragments as the blocking agent was examined using an ELISA system for human carcinoembryonic antigen (hCEA). First, an anti-hCEA MoAb was diluted to 10 μL/mL with 50 mM carbonate buffer (pH 9.6), 100 μL of aliquot was added to a polystyrene immunoplate (E.I.A./R.I.A. 8 Well Strip, supplied from Costar), and then left stand at 37° C. for one hour. After leaving stand, each well was washed three times with 150 μL of the washing solution (PBS(−), 0.05% TWEEN® (polysorbate) 20), subsequently 200 μL of a blocking solution was added, and left stand at 4° C. for 4 hours. As the blocking solution, 2.4 mg of BSA (20 mM Tris-HCl, pH 7.0) generally used and DnaK 419-607 dissolved in the same buffer were used, and 20 mM Tris-HCl (pH 7.0) alone was added as a blank. After removing the blocking solution, 50 μL of an hCEA solution (Immunoflora supplied from Toyobo Co., Ltd.) diluted to 0, 2.5 ng/mL and 5 ng/mL was added, the plate was incubated at 37° C. for one hour, and then washed four times with 150 μL of the washing solution. Subsequently, a peroxidase-labeled anti-hCEA antibody (Immunoflora supplied from Toyobo Co., Ltd.) diluted to an optimal concentration was added, reacted at 37° C. for one hour, and the plate was washed three times with 150 μL of the washing solution (PBS(−), 0.05% TWEEN® (polysorbate) 20). Then, 100 μL of a substrate solution (3,3',5,5'-tetramethylbenzidine, TMBZ) was added to develop a color at 37° C. for 20 minutes with shielding light. Finally, 100 μL of a reaction stop solution (1N $H_2SO_4$) was added, and the developed yellow color was measured at 450 nm/650 nm.

As a result, a linearity was lost in the blank whereas the result with good linearity was obtained in DnaK 419-607 similarly to BSA, and it was shown that DnaK 419-607 of the present invention could be sufficiently applied to the immunological assay (FIG. 12).

EXAMPLE 7

Comparison of Blocking Effects of (Native) DnaK Fragments Without Histidine Tag Since all of the DnaK fragments constructed in Examples 2 to 4 have the histidine tag derived from the expression vector pQE30 at the N terminus, isoelectric points of the DnaK fragments shift to neutral pH. Thus, the DnaK fragments where the histidine tag had been deleted were constructed so as to keep the blocking ability owing to original electrostatic interaction.

The DnaK clone where the histidine tag had been deleted was made using pQE-DnaK 419-607 made in Example 4 as the template and using QuickChange method to delete amino acids after an initiation codon to a DnaK region containing the histidine tag. Actually, using the QuickChange site directive mutagenesis kit (supplied from Stratagene), a BamHI site was introduced upstream of the histidine tag. The manipulation was performed in accordance with instructions thereof. Primer sequences used at that time are shown in SEQ ID NOS:16 and 17. As was also shown in Example 2, an upstream side of the cloned gene has been provided with the BamHI site. Therefore, the clone where the histidine tag was deleted can be obtained by digesting the resulting vector with BamHI and recombining.

This expression vector was designated as pQE-DnaK 419-607N. The native DnaK 419-607 fragment was acquired by culturing transformants obtained by transforming *Escherichia coli* JM109 with this pQE-DnaK 419-607N.

That is, *Escherichia coli* JM109 (pQE-DnaK 419-607N) was inoculated to terrific broth (1.2% polypeptone, 2.4% yeast extract, 0.5% glycerol, 17 mM monopotassium phosphate, 72 mM dipotassium phosphate) containing 100 mg/mL of ampicillin, and cultured at 32° C. for 20 hours with shaking. Microbial cells corresponding to 1 L of this culture were collected by centrifugation, suspended in 200 mL of 100 mM Tris-HCl buffer pH 9.0, and disrupted by French press. Polyethylene imine was added at a final concentration of 0.1% to this disruption solution, heated at 60° C. for 2 hours, and the supernatant was collected by centrifugation. Then, ammonium sulfate with 50% saturation was added, a precipitate was collected by centrifugation, and re-dissolved in 100 mM Tris-HCl buffer, pH 9.0. Furthermore, the solution was heated at 64° C. for 14 hours, and the supernatant was collected by centrifugation. This crude enzyme solution was subjected to SUPERDEX® 200 (supplied from Amersham Bioscience) gel filtration chromatography, then ammonium sulfate with 50% saturation was added, the precipitate was collected by centrifugation, and re-dissolved in 100 mM Tris-HCl buffer, pH 9.0. The solution was desalted by gel filtration chromatography using SEPHADEX® G-25 (supplied from Amersham Bioscience) equilibrated with the same buffer. Subsequently, this DnaK fragment was subjected to the column chromatography using PHENYL SEPHAROSE™ Fast Flow equilibrated with 100 mM Tris-HCl buffer pH 9.0 containing 20% saturated ammonium sulfate, and eluted with a linear gradient of 20 to 0% of saturated ammonium sulfate to acquire a purified DnaK fragment fraction. This purified fragment fraction was condensed by ultrafiltration, and desalted with distilled water to acquire the finally purified DnaK fragment.

The blocking efficiencies of BSA and the native DnaK 419-607 fragment were measured and compared as follows.

First, horseradish peroxidase (PEO-131, supplied from Toyobo Co., Ltd.) for labeling was dissolved at 2 mg/mL in PBS buffer containing BSA or the native DnaK 419-607 fragment. At that time, commercially available BSA (fraction V) was prepared at the concentration of 2 or 10 mg/mL, and the native DnaK 419-607 fragment was prepared at the concentration of 0.1 or 0.5 mg/mL. Then, serial dilutions of 40 to 320 times of the peroxidase dissolution were made using the same solutions, and 100 µL of each dilution was dispensed to a polystyrene 96-well microplate. The plate was left stand at room temperature for one hour, then the solution was removed, and the well was washed with 200 µL of PBS buffer containing 0.02% TWEEN® (polysorbate)20. This washing manipulation was repeated six times, and subsequently the washing solution was thoroughly removed. Then, 100 µL of a tetramethylbenzidine solution (supplied from Bio-Rad) was added, incubated at 37° C. precisely for 10 minutes, and 100 µL of 1N sulfuric acid was added to stop the reaction and develop the color. This developed color was measured by a microplate reader at a major wavelength of 450 nm and a minor wavelength of 650 nm.

Figure 16:
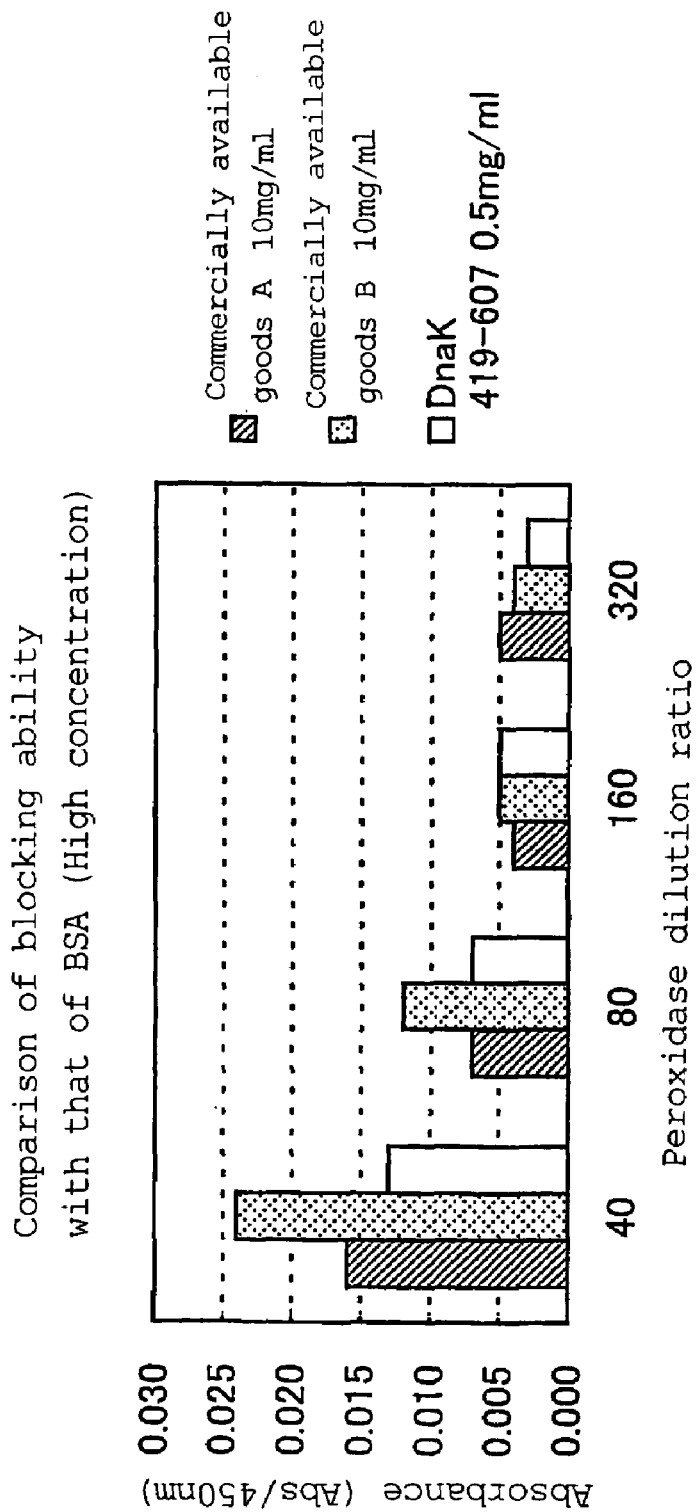
FIG. 16 is a view showing data at high concentrations in FIG. 15.
Figure 17:
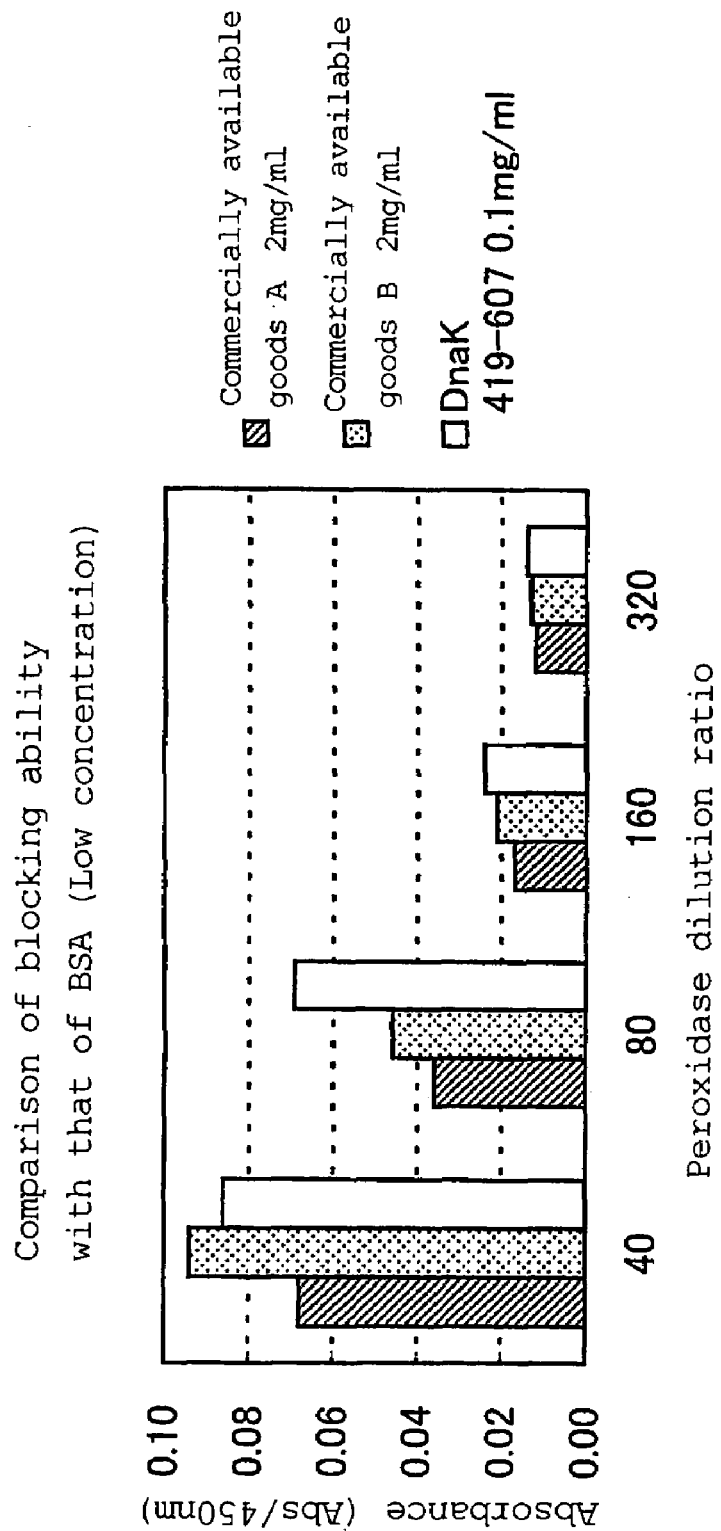
FIG. 17 is a view showing data at low concentrations in FIG. 15.

The results were shown in FIGS. 15 to 17. The native DnaK 416-607 fragment at 1/20 concentration of BSA exhibited inhibition of non-specific color development equivalent to that of BSA, demonstrating that the native DnaK 419-607 fragment exhibits the blocking ability about 20 times of BSA.

INDUSTRIAL APPLICABILITY

In accordance with the present invention, it becomes possible to easily screen the novel protein or the novel partial sequence protein having the blocking ability based on the amino acid sequence data, and produce the protein capable of mass production in *Escherichia coli* and achieving the improved blocking efficiency. In the protein obtained in accordance with the present invention, the blocking ability is high, and the simple and reliable result is obtained compared with the conventional methods. The present invention greatly contributes to clinical diagnosis where the immunoassay is applied and medical practice fields.

---

The invention claimed is:

1. A modified DnaK protein comprising SEQ ID NO: 1, except that:
   (a) the ATPase domain of SEQ ID NO: 1 is deleted, and
   (b) a part of the β-sheet domain of SEQ ID NO: 1 is deleted and/or at least one hydrophilic amino acid in the β-sheet domain of SEQ ID NO: 1 is substituted with a hydrophobic amino acid in order to expose a hydrophobic inside of a β-sheet domain of the DnaK protein,
   wherein the modified DnaK protein has improved blocking efficiency as compared to a DnaK protein consisting of an amino acid sequence from position 384 to a C terminus of SEQ ID NO: 1.

2. The modified DnaK protein of claim 1, wherein the ATPase domain is an amino acid sequence from an N terminus to position 383 of SEQ ID NO: 1.

3. The modified DnaK protein of claim 2, wherein the part of the β-sheet domain is an amino acid sequence from position 384 to at least position 418 and to at most position 472 of SEQ ID NO: 1.

4. The modified DnaK protein of claim 2, wherein the part of the β-sheet domain is an amino acid sequence from position 384 to position 418 of SEQ ID NO: 1.

5. The modified DnaK protein of claim 1, wherein an amino acid sequence from position 608 to a C terminus of SEQ ID NO: 1 is deleted.

6. The modified DnaK protein of claim 1, wherein the at least one hydrophilic amino acid in the β-sheet domain is selected from the group consisting of aspartic acid, glutamic acid, lysine, and arginine.

7. The modified DnaK protein of claim 1, wherein the hydrophobic amino acid is selected from the group consisting of valine, leucine, isoleucine, methionine, phenylalanine, tryptophan, and proline.

8. The modified DnaK protein of claim 1, wherein the at least one hydrophilic amino acid is aspartic acid, and the hydrophobic amino acid is valine.

9. The modified DnaK protein of claim 1, wherein the at least one hydrophilic amino acid is aspartic acid at positions 479 and 481 of SEQ ID NO: 1, and the hydrophobic acid is valine.

10. A composition comprising the modified DnaK protein of claim 1.

11. The composition of claim 10, wherein the composition is a blocking reagent, stabilizing agent, excipient, protein folding accelerator, protein refolding accelerator, coating agent for cell attachment, or coating agent for medical use.

12. A method for producing a modified DnaK protein, the method comprising:
   (a) deleting an ATPase domain of a DnaK protein comprising SEQ ID NO: 1, and
   (b) exposing a hydrophobic inside of a β-sheet domain of the DnaK protein comprising SEQ ID NO: 1 by deleting a part of the β-sheet domain of SEQ ID NO: 1 and/or substituting at least one hydrophilic amino acid in the β-sheet domain of SEQ ID NO: 1 with a hydrophobic amino acid, so as to provide a modified DnaK protein,
   wherein the modified DnaK protein has improved blocking efficiency as compared to a DnaK protein consisting of an amino acid sequence from position 384 to a C terminus of SEQ ID NO: 1.

13. The method of claim 12, wherein the ATPase domain is an amino acid sequence from an N terminus to position 383 of SEQ ID NO: 1.

14. The method of claim 13, wherein the part of the β-sheet domain is an amino acid sequence from position 384 to at least position 418 and to at most position 472 iof SEQ ID NO: 1.

15. The method of claim 14, wherein the part of the β-sheet domain is an amino acid sequence from position 384 to position 418 of SEQ ID NO: 1.

16. The method of claim 12, further comprising:
   (c) deleting an amino acid sequence from position 608 to a C terminus of SEQ ID NO: 1.

17. The method of claim 12, wherein the at least one hydrophilic amino acid in the β-sheet domain is selected from the group consisting of aspartic acid, glutamic acid, lysine, and arginine.

18. The method of claim 12, wherein the hydrophobic amino acid is selected from the group consisting of valine, leucine, isoleucine, methionine, phenylalanine, tryptophan, and proline.

19. The method of claim 12, wherein the at least one hydrophilic amino acid is aspartic acid, and the hydrophobic amino acid is valine.

20. The method of claim 12, wherein the at least one hydrophilic amino acid is aspartic acid at positions 479 and 481 of SEQ ID NO: 1, and the hydrophobic acid is valine.

* * * * *

SEQUENCE LISTING

```
<160> NUMBER OF SEQ ID NOS: 17

<210> SEQ ID NO 1
<211> LENGTH: 638
<212> TYPE: PRT
<213> ORGANISM: Escherichia coli

<400> SEQUENCE: 1

Met Gly Lys Ile Ile Gly Ile Asp Leu Gly Thr Thr Asn Ser Cys Val
1               5                   10                  15

Ala Ile Met Asp Gly Thr Thr Pro Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Phe Lys Ile Ile Ala Ala
                85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160
```

```
Ala Gly Leu Glu Val Lys Arg Ile Ile Asn Glu Pro Thr Ala Ala Ala
                165                 170                 175
Leu Ala Tyr Gly Leu Asp Lys Gly Thr Gly Asn Arg Thr Ile Ala Val
            180                 185                 190
Tyr Asp Leu Gly Gly Gly Thr Phe Asp Ile Ser Ile Ile Glu Ile Asp
        195                 200                 205
Glu Val Asp Gly Glu Lys Thr Phe Glu Val Leu Ala Thr Asn Gly Asp
    210                 215                 220
Thr His Leu Gly Gly Glu Asp Phe Asp Ser Arg Leu Ile Asn Tyr Leu
225                 230                 235                 240
Val Glu Glu Phe Lys Lys Asp Gln Gly Ile Asp Leu Arg Asn Asp Pro
                245                 250                 255
Leu Ala Met Gln Arg Leu Lys Glu Ala Ala Glu Lys Ala Lys Ile Glu
            260                 265                 270
Leu Ser Ser Ala Gln Gln Thr Asp Val Asn Leu Pro Tyr Ile Thr Ala
        275                 280                 285
Asp Ala Thr Gly Pro Lys His Met Asn Ile Lys Val Thr Arg Ala Lys
    290                 295                 300
Leu Glu Ser Leu Val Asp Leu Val Asn Arg Ser Ile Glu Pro Leu
305                 310                 315                 320
Lys Val Ala Leu Gln Asp Ala Gly Leu Ser Val Ser Asp Ile Asp Asp
                325                 330                 335
Val Ile Leu Val Gly Gly Gln Thr Arg Met Pro Met Val Gln Lys Lys
            340                 345                 350
Val Ala Glu Phe Phe Gly Lys Glu Pro Arg Lys Asp Val Asn Pro Asp
        355                 360                 365
Glu Ala Val Ala Ile Gly Ala Ala Val Gln Gly Gly Val Leu Thr Gly
    370                 375                 380
Asp Val Lys Asp Val Leu Leu Leu Asp Val Thr Pro Leu Ser Leu Gly
385                 390                 395                 400
Ile Glu Thr Met Gly Gly Val Met Thr Thr Leu Ile Ala Lys Asn Thr
                405                 410                 415
Thr Ile Pro Thr Lys His Ser Gln Val Phe Ser Thr Ala Glu Asp Asn
            420                 425                 430
Gln Ser Ala Val Thr Ile His Val Leu Gln Gly Glu Arg Lys Arg Ala
        435                 440                 445
Ala Asp Asn Lys Ser Leu Gly Gln Phe Asn Leu Asp Gly Ile Asn Pro
    450                 455                 460
Ala Pro Arg Gly Met Pro Gln Ile Glu Val Thr Phe Asp Ile Asp Ala
465                 470                 475                 480
Asp Gly Ile Leu His Val Ser Ala Lys Asp Lys Asn Ser Gly Lys Glu
                485                 490                 495
Gln Lys Ile Thr Ile Lys Ala Ser Ser Gly Leu Asn Glu Asp Glu Ile
            500                 505                 510
Gln Lys Met Val Arg Asp Ala Glu Ala Asn Ala Glu Ala Asp Arg Lys
        515                 520                 525
Phe Glu Glu Leu Val Gln Thr Arg Asn Gln Gly Asp His Leu Leu His
    530                 535                 540
Ser Thr Arg Lys Gln Val Glu Glu Ala Gly Asp Lys Leu Pro Ala Asp
545                 550                 555                 560
Asp Lys Thr Ala Ile Glu Ser Ala Leu Thr Ala Leu Glu Thr Ala Leu
                565                 570                 575
Lys Gly Glu Asp Lys Ala Ala Ile Glu Ala Lys Met Gln Glu Leu Ala
```

```
                580             585              590
         Gln Val Ser Gln Lys Leu Met Glu Ile Ala Gln Gln His Ala Gln
                     595                 600                 605

Gln Gln Thr Ala Gly Ala Asp Ala Ser Ala Asn Asn Ala Lys Asp Asp
                 610                 615                 620

Asp Val Asp Ala Glu Phe Glu Glu Val Lys Asp Lys Lys
         625                 630                 635

<210> SEQ ID NO 2
<211> LENGTH: 1917
<212> TYPE: DNA
<213> ORGANISM: Escherichia coli

<400> SEQUENCE: 2
atgggtaaaa taattggtat cgacctgggt actaccaact cttgtgtagc gattatggat      60
ggcaccactc ctcgcgtgct ggagaacgcc gaaggcgatc gcaccacgcc ttctatcatt     120
gcctataccc aggatggtga aactctagtt ggtcagccgg ctaaacgtca ggcagtgacg     180
aacccgcaaa acactctgtt tgcgattaaa cgcctgattg gtcgccgctt ccaggacgaa     240
gaagtacagc gtgatgtttc catcatgccg ttcaaaatta ttgctgctga taacggcgac     300
gcatgggtcg aagttaaagg ccagaaaatg caccgccgc agatttctgc tgaagtgctg     360
aaaaaaatga gaaaaccgc tgaagattac ctgggtgaac cggtaactga agctgttatc     420
accgtaccgg catactttaa cgatgctcag cgtcaggcaa ccaaagacgc aggccgtatc     480
gctggtctgg aagtaaaacg tatcatcaac gaaccgaccg cagctgcgct ggcttacggt     540
ctggacaaag cactggcaa ccgtactatc gcggtttatg acctgggtgg tggtactttc     600
gatatttcta ttatcgaaat cgacgaagtt gacggcgaaa aaaccttcga agttctggca     660
accaacggtg atacccacct gggggtgaa gacttcgaca ccgtctgat caactatctg     720 gttgaagaat caagaaaga tcagggcatt gacctgcgca cgatccgct ggcaatgcag     780 cgcctgaaag aagcggcaga aaagcgaaa tcgaactgt cttccgctca gcagaccgac     840
gttaacctgc catacatcac tgcagacgcg accggtccga acacatgaa catcaaagtg     900 actcgtgcga aactggaaag cctggttgaa gatctggtaa accgttccat tgagccgctg     960
aaagttgcac tgcaggacgc tggcctgtcc gtatctgata tcgacgacgt tatcctcgtt    1020
ggtggtcaga ctcgtatgcc aatggttcag aagaaagttg ctgagttctt tggtaaagag    1080
ccgcgtaaag acgttaaccc ggacgaagct gtagcaatcg tgctgctgt tcagggtggt    1140 gttctgactg gtgacgtaaa agacgtactg ctgctggacg ttaccccgct gtctctgggt    1200
atcgaaacca tgggcggtgt gatgacgacg ctgatcgcga aaaacaccac tatccccgacc   1260 aagcacagcc aggtgttctc taccgctgaa gacaaccagt ctgcggtaac catccatgtg    1320
ctgcagggtg aacgtaaacg tgcggctgat aacaaatctc tgggtcagtt caacctagat    1380
ggtatcaacc cggcaccgcg cggcatgccg cagatcgaag ttaccttcga tatcgatgct    1440
gacggtatcc tgcacgtttc cgcgaaagat aaaaacagcg gtaaagagca agatcacc     1500 atcaaggctt cttctggtct gaacgaagat gaaatccaga aatggtacg cgacgcagaa    1560 gctaacgccg aagctgaccg taagtttgaa gagctggtac agactcgcaa ccagggcgac    1620
catctgctgc acagcacccg taagcaggtt gaagaagcag gcgacaaact gccggctgac    1680
gacaaaactg ctatcgagtc tgcgctgact gcactggaaa ctgctctgaa aggtgaagac    1740
aaagccgcta tcgaagcgaa aatgcaggaa ctggcacagg tttcccagaa actgatggaa    1800
```

```
atcgcccagc agcaacatgc ccagcagcag actgccggtg ctgatgcttc tgcaaacaac    1860
gcgaaagatg acgatgttgt cgacgctgaa tttgaagaag tcaaagacaa aaaataa       1917
```

<210> SEQ ID NO 3
<211> LENGTH: 55
<212> TYPE: DNA
<213> ORGANISM: Artificial
<220> FEATURE:
<223> OTHER INFORMATION: Synthetic DNA

<400> SEQUENCE: 3

```
gcggatccat cgagggtaga ggtgacgtaa aagacgtact gctgctggac gttac          55
```

<210> SEQ ID NO 4
<211> LENGTH: 33
<212> TYPE: DNA
<213> ORGANISM: Artificial
<220> FEATURE:
<223> OTHER INFORMATION: Synthetic DNA

<400> SEQUENCE: 4

```
ttatttttg tctttgactt cttcaaattc agc                                   33
```

<210> SEQ ID NO 5
<211> LENGTH: 30
<212> TYPE: DNA
<213> ORGANISM: Artificial
<220> FEATURE:
<223> OTHER INFORMATION: Synthetic DNA

<400> SEQUENCE: 5

```
gccggctgac gactaaactg ctatcgagtc                                      30
```

<210> SEQ ID NO 6
<211> LENGTH: 30
<212> TYPE: DNA
<213> ORGANISM: Artificial
<220> FEATURE:
<223> OTHER INFORMATION: Synthetic DNA

<400> SEQUENCE: 6

```
gactcgatag cagtttagtc gtcagccggc                                      30
```

<210> SEQ ID NO 7
<211> LENGTH: 30
<212> TYPE: DNA
<213> ORGANISM: Artificial
<220> FEATURE:
<223> OTHER INFORMATION: Synthetic DNA

<400> SEQUENCE: 7

```
tgctctgaaa ggttaagaca aagccgctat                                      30
```

<210> SEQ ID NO 8
<211> LENGTH: 30
<212> TYPE: DNA
<213> ORGANISM: Artificial
<220> FEATURE:
<223> OTHER INFORMATION: Synthetic DNA

<400> SEQUENCE: 8

```
atagcggctt tgtcttaacc tttcagagca                                      30
```

<210> SEQ ID NO 9
<211> LENGTH: 30

<212> TYPE: DNA
<213> ORGANISM: Artificial
<220> FEATURE:
<223> OTHER INFORMATION: Synthetic DNA

<400> SEQUENCE: 9
gcagcaacat gcctaacagc agactgccgg                                        30

<210> SEQ ID NO 10
<211> LENGTH: 30
<212> TYPE: DNA
<213> ORGANISM: Artificial
<220> FEATURE:
<223> OTHER INFORMATION: Synthetic DNA

<400> SEQUENCE: 10
ccggcagtct gctgttaggc atgttgctgc                                        30

<210> SEQ ID NO 11
<211> LENGTH: 30
<212> TYPE: DNA
<213> ORGANISM: Artificial
<220> FEATURE:
<223> OTHER INFORMATION: Synthetic DNA

<400> SEQUENCE: 11
ccttcgatat cgttgctgtc ggtatcctgc                                        30

<210> SEQ ID NO 12
<211> LENGTH: 30
<212> TYPE: DNA
<213> ORGANISM: Artificial
<220> FEATURE:
<223> OTHER INFORMATION: Synthetic DNA

<400> SEQUENCE: 12
gcaggatacc gacagcaacg atatcgaagg                                        30

<210> SEQ ID NO 13
<211> LENGTH: 27
<212> TYPE: DNA
<213> ORGANISM: Artificial
<220> FEATURE:
<223> OTHER INFORMATION: Synthetic DNA

<400> SEQUENCE: 13
tctggatcca acgaagatga aatccag                                           27

<210> SEQ ID NO 14
<211> LENGTH: 30
<212> TYPE: DNA
<213> ORGANISM: Artificial
<220> FEATURE:
<223> OTHER INFORMATION: Synthetic DNA

<400> SEQUENCE: 14
gcggatccgc tgaccgtaag tttgaagagc                                        30

<210> SEQ ID NO 15
<211> LENGTH: 29
<212> TYPE: DNA
<213> ORGANISM: Artificial
<220> FEATURE:
<223> OTHER INFORMATION: Synthetic DNA

<400> SEQUENCE: 15

-continued

```
ccggatcccc gaccaagcac agccaggtg                                    29

<210> SEQ ID NO 16
<211> LENGTH: 29
<212> TYPE: DNA
<213> ORGANISM: Artificial
<220> FEATURE:
<223> OTHER INFORMATION: Synthetic DNA

<400> SEQUENCE: 16
attaactatg agaggatccc atcaccatc                                    29

<210> SEQ ID NO 17
<211> LENGTH: 29
<212> TYPE: DNA
<213> ORGANISM: Artificial
<220> FEATURE:
<223> OTHER INFORMATION: Synthetic DNA

<400> SEQUENCE: 17
gatggtgatg ggatcctctc atagttaat                                    29
```